(12) United States Patent
Evans et al.

(10) Patent No.: US 11,420,002 B2
(45) Date of Patent: Aug. 23, 2022

(54) NASAL CANNULA

(71) Applicant: Fisher & Paykel Healthcare Limited, Auckland (NZ)

(72) Inventors: Alicia Jerram Hunter Evans, Auckland (NZ); Craig Karl White, Auckland (NZ); Samantha Dale Oldfield, Auckland (NZ); Milanjot Singh Assi, Auckland (NZ); Erik Robertus Scheirlinck, Auckland (NZ); Callum James Thomas Spence, Auckland (NZ); Laurence Gulliver, Auckland (NZ); Dexter Chi Lun Cheung, Auckland (NZ); Michael Robert Barraclough, Auckland (NZ); Matthew Jon Payton, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 433 days.

(21) Appl. No.: 15/559,785

(22) PCT Filed: Mar. 31, 2016

(86) PCT No.: PCT/IB2016/051817
§ 371 (c)(1),
(2) Date: Sep. 19, 2017

(87) PCT Pub. No.: WO2016/157103
PCT Pub. Date: Oct. 6, 2016

(65) Prior Publication Data
US 2018/0064898 A1    Mar. 8, 2018

Related U.S. Application Data

(60) Provisional application No. 62/140,776, filed on Mar. 31, 2015, provisional application No. 62/140,836, filed on Mar. 31, 2015.

(51) Int. Cl.
*A61M 16/06* (2006.01)
*A61M 15/08* (2006.01)
(Continued)

(52) U.S. Cl.
CPC ..... *A61M 16/0666* (2013.01); *A61B 1/00165* (2013.01); *A61B 1/2676* (2013.01);
(Continued)

(58) Field of Classification Search
CPC .......... A61M 16/0666; A61M 16/0875; A61M 15/08; A61M 16/14; A61M 11/06; A61M 16/0672
See application file for complete search history.

(56) References Cited

U.S. PATENT DOCUMENTS 3,874,380 A * 4/1975 Baum ............... A61M 15/0028
128/200.14
4,602,644 A * 7/1986 DiBenedetto .......... A61B 5/087
128/207.18
(Continued)

FOREIGN PATENT DOCUMENTS

EP 2231244 B1 6/2016
WO WO 2003/068301 8/2003
(Continued)

OTHER PUBLICATIONS

Supplementary Partial European Search Report for EP Appl. No. 16771499 dated Sep. 12, 2018 in 4 pages.
(Continued)

*Primary Examiner* — Joseph D. Boecker
*Assistant Examiner* — Thomas W Greig
(74) *Attorney, Agent, or Firm* — Knobbe, Martens, Olson & Bear, LLP

(57) ABSTRACT

The disclosure relates to a nasal cannula comprising a port configured for delivery of a medicament into a flow of a fluid
(Continued)

being delivered by the nasal cannula to a user and/or configured for interfacing with a medicament delivery device or an instrument. The disclosure also relates to a nasal cannula comprising an asymmetric profile to reduce an amount of occlusion of one nare of a user to provide access for an instrument to the nare with the nasal cannula in use.

20 Claims, 19 Drawing Sheets

(51) Int. Cl.
    *A61B 1/00*           (2006.01)
    *A61B 1/267*         (2006.01)
    *A61B 1/273*         (2006.01)
    *A61M 11/06*        (2006.01)
    *A61M 16/08*        (2006.01)
    *A61M 16/14*        (2006.01)
    *A61M 16/20*        (2006.01)
    *A61M 16/04*        (2006.01)

(52) U.S. Cl.
    CPC ............ *A61B 1/2733* (2013.01); *A61M 11/06* (2013.01); *A61M 15/08* (2013.01); *A61M 16/0672* (2014.02); *A61M 16/0875* (2013.01); *A61M 16/14* (2013.01); *A61M 16/0488* (2013.01); *A61M 16/0683* (2013.01); *A61M 16/0816* (2013.01); *A61M 16/147* (2014.02); *A61M 16/201* (2014.02); *A61M 2206/14* (2013.01); *A61M 2210/0618* (2013.01)

(56) References Cited

U.S. PATENT DOCUMENTS

| | | | |
|---|---|---|---|
| 5,335,656 A * | 8/1994 | Bowe ...................... | A61B 5/097 128/206.11 |
| 5,752,511 A | 5/1998 | Simmons et al. | |
| 5,996,579 A * | 12/1999 | Coates .............. | A61M 16/0084 128/202.27 |
| 9,333,317 B2 * | 5/2016 | Cortez, Jr. ......... | A61M 16/0672 |
| 10,086,161 B1 * | 10/2018 | Rashidi ............. | A61M 16/0666 |
| 2002/0059935 A1 * | 5/2002 | Wood ................ | A61M 16/0666 128/207.18 |
| 2003/0079749 A1 * | 5/2003 | Strickland ......... | A61M 16/0666 128/203.22 |
| 2003/0200970 A1 | 10/2003 | Stenzler et al. | |
| 2004/0015092 A1 * | 1/2004 | Pettersson ......... | A61M 16/0666 600/532 |
| 2005/0045182 A1 * | 3/2005 | Wood ................ | A61M 16/0666 128/207.18 |
| 2007/0175473 A1 | 8/2007 | Lewis et al. | |
| 2008/0047559 A1 * | 2/2008 | Fiori ................. | A61M 16/0666 128/206.11 |
| 2009/0044808 A1 * | 2/2009 | Guney ................ | A61M 16/06 128/206.24 |
| 2009/0299158 A1 * | 12/2009 | Boatner ................ | A61B 5/01 600/301 |
| 2010/0168601 A1 * | 7/2010 | Adriance ............... | A61B 5/087 600/537 |
| 2010/0252044 A1 * | 10/2010 | Duquette .......... | A61M 16/0666 128/204.25 |
| 2011/0000487 A1 | 1/2011 | Moa et al. | |
| 2011/0094518 A1 * | 4/2011 | Cipollone ......... | A61M 16/0858 128/207.18 |
| 2011/0257550 A1 * | 10/2011 | Choi ..................... | A61B 5/097 600/532 |
| 2011/0284001 A1 * | 11/2011 | Tero .................. | A61M 16/0666 128/204.18 |
| 2012/0111331 A1 * | 5/2012 | Witt .................. | A61M 16/0666 128/205.25 |
| 2012/0150119 A1 * | 6/2012 | Schaeffer ........... | A61B 17/3468 604/164.06 |
| 2013/0152925 A1 * | 6/2013 | Rahmel ................. | A61M 16/12 128/203.12 |
| 2013/0211275 A1 * | 8/2013 | Curti ................. | A61M 16/0666 600/543 |
| 2014/0150789 A1 * | 6/2014 | Flanagan .......... | A61M 16/1005 128/203.22 |
| 2014/0158127 A1 * | 6/2014 | Boucher ........... | A61M 16/0666 128/203.22 |
| 2015/0000660 A1 * | 1/2015 | Martin ................ | A61M 16/125 128/203.22 |
| 2015/0000661 A1 | 1/2015 | Martin | |
| 2015/0000673 A1 | 1/2015 | Martin | |
| 2016/0158476 A1 * | 6/2016 | Tatkov .............. | A61M 16/0683 128/203.22 |

FOREIGN PATENT DOCUMENTS

| | | |
|---|---|---|
| WO | WO 2008/060587 | 5/2008 |
| WO | WO 2011/110961 | 9/2011 |
| WO | WO 2012/020004 | 2/2012 |
| WO | WO 2014/042862 | 3/2014 |
| WO | WO 2014/089188 | 6/2014 |
| WO | WO 2014/091362 | 6/2014 |
| WO | WO 2014/142681 | 9/2014 |
| WO | WO 2015/020540 | 2/2015 |
| WO | WO 2016/157103 | 10/2016 |

OTHER PUBLICATIONS

International Search Report and Written Opinion for PCT/ IB2016/ 051817 dated Jun. 24, 2016 in 9 pages.
Supplementary European Search Report for EP Application No. 16771499 dated Jan. 22, 2019 in 7 pages.
Office Action in corresponding European Patent Application No. 16771499.7, dated Mar. 16, 2020, in 3 pages.
Examination Report in corresponding Australian Patent Application No. 2016242103, dated Sep. 8, 2020, in 6 pages.

* cited by examiner

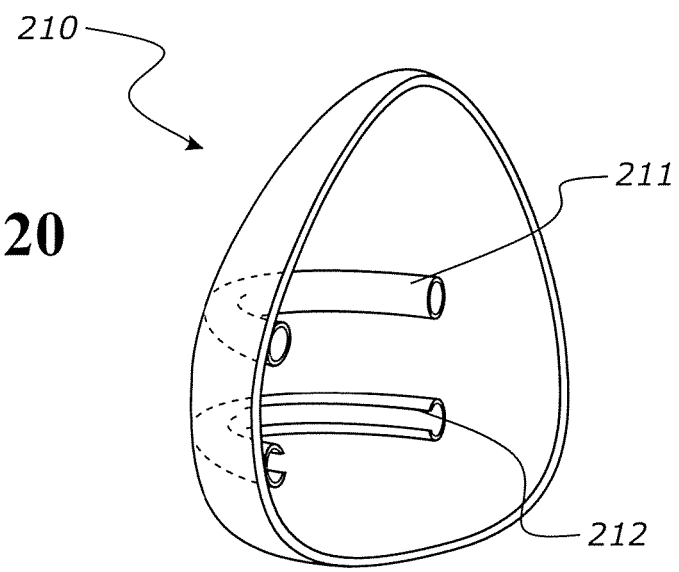
FIGURE 20
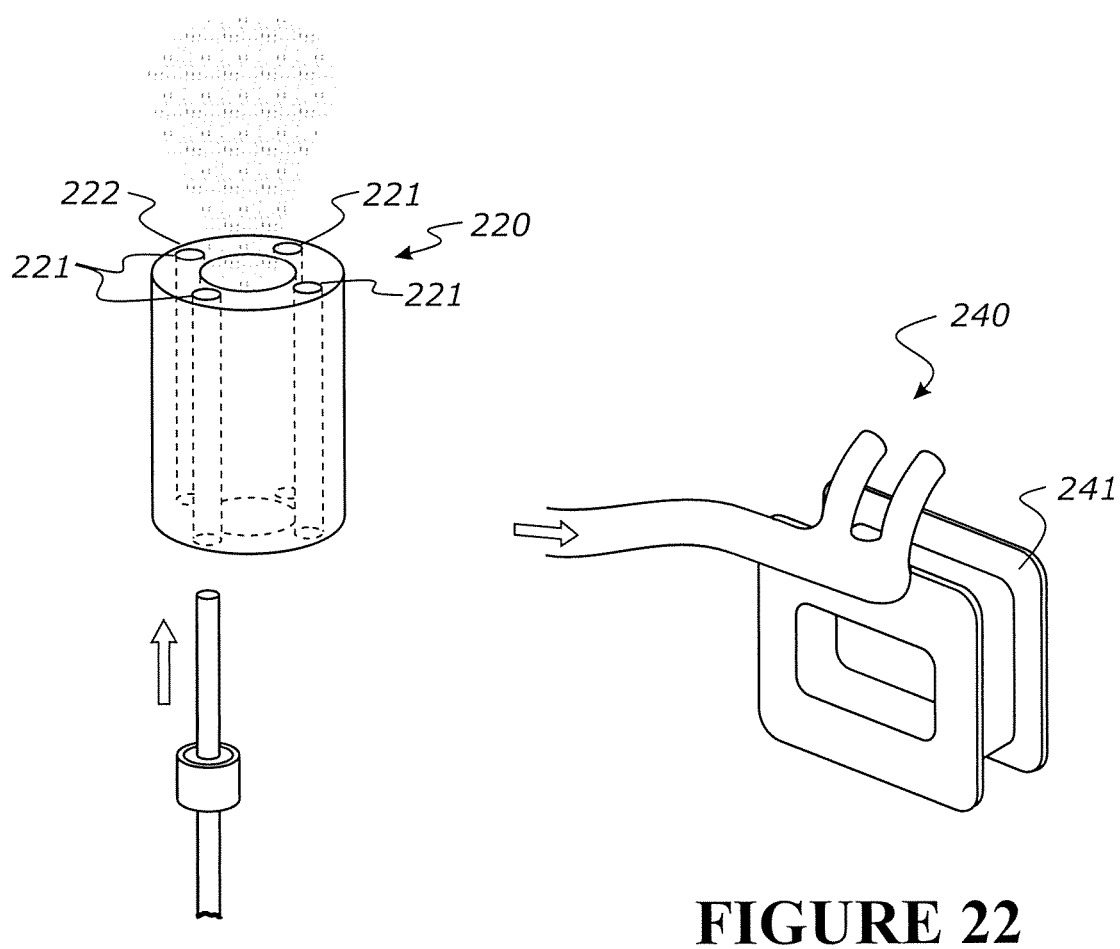
FIGURE 21
FIGURE 22

NASAL CANNULA

BACKGROUND

Field of the Disclosure

The present disclosure generally relates to nasal cannulas for providing a flow of respiratory gases to a patient, and particularly nasal cannulas for interfacing with an airway instrument and/or a medicament dispensing device, and/or cannulas that allow redirecting or controlling of gas flow.

Description of the Related Art

Patients may lose respiratory function during anaesthesia, or sedation, or more generally during certain medical procedures. Prior to a medical procedure a patient may be pre-oxygenated by a medical professional to provide a reservoir of oxygen saturation, and this pre-oxygenation is generally carried out with a bag and a face mask. Once under general anaesthesia, patients must be intubated to ventilate the patient. In some cases, intubation is completed in 30 to 60 seconds, but in other cases, particularly if the patient's airway is difficult to traverse (for example, due to cancer, severe injury, obesity or spasm of the neck muscles), intubation will take significantly longer. While pre-oxygenation provides a buffer against declines in oxygen saturation, for long intubation procedures, it is necessary to interrupt the intubation process and reapply the face mask to increase the patient's oxygen saturation to adequate levels. The interruption of the intubation process may happen several times for difficult intubation processes, which is time consuming and puts the patient at severe health risk. After approximately three attempts at intubation the medical procedure will be abandoned.

A nasal cannula is used to provide a flow of gases to a patient or user via the patient's or user's nasal passages. A nasal cannula typically has two prongs, each prong adapted to fit within a patient's nostril. In certain procedures that require intubation, for example in general anesthesia where a patient is not spontaneously breathing, the insertion of instruments or tubes into a patient's airway may be obstructed or prevented if a nasal cannula were to be used simultaneously with other airway instruments. In some situations, it may be desirable to use a nasal cannula simultaneously with other airway devices or instruments. For example, respiratory gases provided at high flow rates can deliver a level of pressure that may help to keep a patient's airway open. Therefore it may be desirable to use a high flow cannula on a patient to maintain a patent airway during anesthesia, where intubation of a tube or other instrument via the patient's nasal passage is necessary.

Delivery of drugs (i.e. medicament) to a user or patient's airway or parts of their airway may be required for particular reasons. Various medicaments can be sprayed or administered into the airway, but the medicament may not reach the desired location, or a useful topical application of such medicament across the airway may not be achieved.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY

It is therefore an object of this disclosure to provide a cannula which will go at least some way towards addressing the foregoing problems or which will at least provide the industry or public with a useful choice.

In accordance with at least one of the embodiments disclosed herein, a nasal cannula comprises a port configured for delivery of a medicament into a flow of a fluid being delivered by the nasal cannula to a user and/or configured for interfacing with a medicament delivery device or an instrument.

The port may comprise a guide for directing a flow of medicament into the flow of fluid, or for directing the medicament delivery device or the instrument into the nasal cannula and/or the user's airway.

The guide may provide for a pre-determined geometry of the port to direct, locate or position the medicament delivery device or instrument or an outlet of the medicament delivery device or instrument at a desired angle or orientation relative to the nasal cannula.

The guide may be configured to provide a clearance between the guide and the medicament delivery device or the instrument.

The nasal cannula may comprise at least one nasal prong or a pair of nasal prongs.

The port may be located upon a nasal prong of the nasal cannula, or wherein the interface comprises two ports, each port located upon each of a pair of nasal prongs.

Alternatively the port may be located on a manifold part of the nasal cannula.

The port may be located on the manifold part so that a path through the port is aligned with a flowpath through a nasal prong of the nasal cannula.

The port may be arranged to face away from the patient's face in use. For example the port may be provided on a wall of the cannula that faces away from the face of a patient in use.

The nasal cannula may comprise a moulded or otherwise shaped region suitable for accepting or receiving or locating or seating of the medicament delivery device or the instrument relative to the port.

With the medicament delivery device or the instrument in-situ with the port, the port may seal about the medicament delivery device or the instrument.

The port may comprise a closable or re-closable opening.

The port may comprise of a self-closing seal.

The port may include a relatively rigid component to support the medicament delivery device or the instrument when in-situ with the port.

The cannula may include structures or elements for an in-line atomisation or nebulisation of medicament dispensed or administered or delivered via said port.

The port may include the structures or elements for an in-line atomisation or nebulisation of medicament dispensed or administered or delivered via said port.

The structures or elements may be ribs or serrations within the nasal prong.

The port may be a channel in an outer surface of a nasal prong of the nasal cannula.

A nasal prong of the cannula may be a multi-lumen prong, and wherein one of said lumen may provide the port for inserting the medicament delivery device or instrument.

The nasal cannula may comprise a medicament supply tube extending from the port.

The supply tube may extend from the port to an outlet end of a nasal prong of the nasal cannula.

An outlet end of the tube may be located at an inward side of the nasal prong to be located adjacent to the patient's septum in use.

The supply tube may be formed within a wall of a nasal prong of the nasal cannula.

The supply tube may be located within a lumen of a nasal prong of the cannula.

The supply tube may be located approximately centrally within the lumen of the nasal prong of the nasal cannula.

The port may be an inlet end of the supply tube.

An inlet end of the supply tube may extend from a manifold of the cannula so that the medicament delivery device may be connected to the port remotely from the manifold.

The supply tube may comprise a small diameter outlet, such that the outlet operates as a nozzle to spray or otherwise disperse the medicament from the supply tube.

The port may be adapted to receive a nozzle or outlet of the medicament delivery device or to be received in a nozzle or outlet of the medicament delivery device.

The instrument may be an airway tube or conduit, an introducer/bougie, a stylet, a guide, a tube exchanger, or a scope or diagnostics instrument such as an endoscope, a rigid or flexible bronchoscope, an esophagoscope or a fibreoptic scope.

The relatively more rigid component may provide a surface for positive orientation or definition of a secure location or seating position for a dispenser.

The relatively more rigid component may provide for a pre-determined angle of insertion by the dispenser to the port.

The port may comprise a relatively softer or more flexible or compressible component that seals over the port.

The port may comprise a covering of a relatively elastic or elasticated cover material that stretches when the dispenser is inserted and allows extension, optionally a seal is said elastic or elasticated cover material.

The port may be formed of a combination of a relatively more rigid component and a covering material of at least one layer of a relatively compressible material.

The port may allow for insertion of a relatively long medicament dispenser or instrument.

The relatively long medicament dispenser or instrument may be a conduit or tube to be extended to project along at least a length of or through the flowpath of the patient interface or a component such as a gas supply conduit associated with the interface.

The dispenser when in-situ with the port, may provide for a medicament dispenser outlet termination at the flowpath outlet from one or more of said nasal prongs, or said a medicament dispenser outlet may terminate within the flowpath (i.e. upstream of the flowpath outlet from one or more nasal prongs) or may terminate at a position beyond the flowpath outlet of the one or more nasal prongs (i.e. downstream of the flowpath outlet from the one or more nasal prongs).

Insertion or connection of the medicament dispenser with the port may promote a protrusion (e.g. such as a lumen provided) to extend along and through the flowpath.

Insertion of the dispenser may promote the protrusion to extend from the port along and through the flowpath and along and through one or more nasal prongs.

The protrusion may further comprise corrugations or other concertina-type arrangements that can unfold and extend to allow an extension or lengthening of the protrusion.

Extension of the protrusion may allow for an outlet of the protrusion to extend beyond or past the end of one or a pair of nasal prongs, or other structures associated with a patient interface.

The protrusion may be curved or shaped or configured for nasal anatomical fit.

The protrusion in an extended configuration may reduce, minimise or prevent flow of gases along the flowpath, optionally the protrusion may reduce, minimise or prevent flow of gases through a nasal prong or prongs.

A pressure relief system or, device or arrangement may be associated with the flowpath for relief of pressure above a pre-determined pressure level.

A recirculation system or scavenging system may be combined with the interface for collection of gases from the flowpath not delivered to the user, or which are exhaled by the user, said gases to be filtered and returned to the user (e.g. non-administered medicament may be retrieved and returned to the user).

One or a pair of nasal prongs may be relatively long, such that one or each nasal prong may extend relatively deep into a user's nasal cavity, optionally, one or both nasal prongs may be curved to conform to nasal geometry.

There may be provided a patient interface, such as a nasal cannula, comprising one or a pair of nasal prongs that may be extendable or comprise portions or protrusions extendible in length.

A nasal prong comprises an inner secondary prong portion (such as a protrusion) including corrugations or concertina-type sections for lengthening of the inner secondary prong portion (or said protrusion).

The dispenser may comprise a reservoir of pre-formulated medicament of a pre-determined quantity, optionally in a ready-to-dispense configuration.

The patient interface, or a component associated with the patient interface (such as a gas supply conduit) may comprise one or more reservoirs for receiving and/or storing of a medicament.

The reservoir may be actuated mechanically, electronically or manually or by other forms to controllably release medicament into a flowpath.

In accordance with at least one of the embodiments disclosed herein, a patient interface comprises at least one gas delivery element (such as a nasal prong in a nasal cannula), wherein said gas delivery element is sized or shaped so as to provide for in-line atomisation or nebulisation of a medicament to be delivered to a user through a gas flowpath.

A nasal prong may be a gas delivery element, said nasal prong comprising a relatively small internal diameter, or other internal structures in the gas flowpath, so as to create high gas velocities in the gas flowpath through the prong.

Multiple gas delivery elements may be provided, each such element providing for a separate gas flowpath for medicament dispensing, delivery or administration.

The gas delivery element may be a nasal prong.

In accordance with at least one of the embodiments disclosed herein, a nasal cannula comprises one or a pair of nasal prongs, one or each of said nasal prongs comprising of a shaped or otherwise curved region for accommodating a medicament dispenser adjacent to said prong when in the nare of a user's nose.

In accordance with at least one of the embodiments disclosed herein, an apparatus for delivering a medicament to a user comprising a medicament delivery device or instrument and a nasal cannula as described in any one or more of the above statements, the port and the medicament delivery device or instrument complementarily adapted such that with the medicament delivery device or instrument in-situ with the port an outlet of the medicament delivery device or instrument is located: (i) at an outlet of a nasal prong of the nasal cannula, or (ii) at a small distance beyond the outlet of a nasal prong downstream of the nasal cannula.

The apparatus may comprise the medicament delivery device and wherein the medicament delivery device may comprise a reservoir of pre-formulated medicament of a pre-determined quantity, optionally in a ready-to-dispense configuration.

In accordance with at least one of the embodiments disclosed herein a, nasal cannula may comprise an asymmetric profile to reduce an amount of occlusion of one nare of the user to provide access for an instrument to the nare with the nasal cannula in use.

The cannula may be asymmetric in plan view and/or when viewed from the front. The cannula may have a frame or manifold part and one nasal prong or a pair of nasal prongs extending from the frame or manifold part, and the frame or manifold part may be asymmetrical.

The frame or manifold part may have a thickness extending between a backside of the cannula that locates against or adjacent the user's face below the user's nose and an opposite outwards front side of the cannula, and the thickness adjacent one nare of the user may be less than the thickness adjacent the other nare of the user.

The frame or manifold part may have a height extending between a top of the frame or manifold part and a bottom of the frame or manifold part, and the height adjacent one nare of the user may be less than the height adjacent the other nare of the user.

The nasal cannula may comprise a pair of nasal prongs and wherein one of the pair of nasal prongs may have an oval cross section or a cross section shaped flatter than a circle to provide a space between the prong and the user's nare for an instrument to be inserted into the nare.

The nasal cannula may comprise a pair of gas outlets, a first gas outlet of the pair of gas outlets being a nasal prong and a second gas outlet of the pair of gas outlets being prong-less or a second nasal prong that may be shorter than the nasal prong of the first gas outlet.

The nasal cannula may comprise a manifold part that receives a flow of gases and redistributes that flow to each nare of a user via a pair of outlets or apertures, each outlet corresponding with a nare of the user, wherein the outlets or apertures may be prong-less.

In accordance with at least one of the embodiments disclosed herein, a nasal cannula comprises two nasal prongs of unequal length.

A shorter one of the prongs may be of a length to have a relatively minimal or substantially no extension into the nare of a patient in use.

In accordance with at least one of the embodiments disclosed herein, a nasal cannula comprises two nasal prongs, wherein in each prong is of a length to have minimal or substantially no extension into the nares of the patient.

In accordance with at least one of the embodiments disclosed herein, a cannula is asymmetric to be reduced in size on one side compared to an opposite side.

The cannula may be asymmetrical to reduce an amount of occlusion of the user's nare on the side of the cannula that is reduced in size.

The cannula may be asymmetrical to provide access to a nare of a user at a side of the cannula that is reduced in size while the cannula is in use and while the cannula provides flow to at least the other nare, or both nares.

The cannula may be asymmetric in plan view.

The cannula may be asymmetric when viewed from the front.

The cannula may be asymmetric when viewed from the front of the cannula and also when viewed in plan view.

The cannula may have a frame or manifold part and two nasal prongs extending from the frame or manifold part.

The frame or manifold part may be asymmetrical.

The nasal prong at the side of the cannula that is reduced in size may be oval or a shape that is flatter than a circle to provide a space between the prong and the user's nare for an instrument to be inserted.

The asymmetrical cannula may comprise two prongs, or one prong and a prong-less outlet on the reduced in size side of the cannula.

The prong on the reduced in size side of the cannula may be shorter than the prong on the other side of the cannula.

In accordance with at least one of the embodiments disclosed herein, a cannula comprises a manifold part or frame that receives a flow of gases and redistributes that flow to each nare of a user via two outlets or apertures, each outlet corresponding with a nare of the user, wherein the outlets or apertures are prongless.

In accordance with at least one of the embodiments disclosed herein, a nasal cannula comprises a removable or extendable prong.

At least one prong may be retractable into or extendable from a manifold of the cannula, for example the prong slides into and out of the manifold of the cannula.

One or both prongs of the cannula may comprise corrugations or concertina type sections which can be extended by a user to lengthen to extend the length of the prong. The corrugations may be formed at a base of the prong, or partway or fully along the length of the prong.

One or both prongs may be configured to be torn from a manifold part of the cannula.

One or both nasal prongs may be removably attached to a manifold part of the cannula. The releasable prong may be permanently attached to the cannula assembly, for example by a lanyard or leash.

In accordance with at least one of the embodiments disclosed herein, a nasal cannula comprises a moveable prong that may be moved out of alignment from a user's nare, while a second prong remains in fluid communication with the other nare of the user.

The cannula may comprise a prong that may be slidable relative to the other prong or to a manifold part of the cannula, to displace the prong from a user's nare in use.

The nasal cannula may comprise a gas supply rail or conduit (manifold part), and one prong may be slidable on the manifold part. The slidable prong may comprise a prong portion to be inserted into a nare of the user, and a base portion adapted to receive the manifold part to slide thereon. The manifold may comprise an aperture that is exposed when the prong is slid out of alignment with a user's nare, to provide some gas flow from the manifold to the exposed nare of the user.

In accordance with at least one of the embodiments disclosed herein, a cannula is configured to optionally provide flow to one nare of a user while providing flow to the other nare of the user.

The cannula may comprise one nasal prong to provide a flow of gas to a nare of a user, and an opening or aperture in a manifold of the nasal cannula that may be capped or plugged by a cap.

The cannula may comprise a rotatable cuff to block or unblock an opening or aperture on a manifold of the cannula to optionally provide a flow of gas to one nare of the user. The rotatable cuff may have an aperture to align with the manifold aperture to allow flow from the manifold aperture to the user's nare.

Flow to one nare may be optionally provided via a nasal prong.

A nasal cannula may comprise a rotatable prong, may be rotatable on a gas supply rail or conduit or manifold part of the cannula (herein called a manifold part) between a open position and a closed position. In the closed configuration the prong may be rotated so that the prong is not in fluid communication with the manifold and is out of alignment with the user's nare. In the closed configuration, 100% of the flow may be directed via a second prong into one nare of the user.

Both prongs may be rotatable on a rail or supply conduit or manifold of the cannula.

A nasal cannula may comprise a slidable prong, the slidable prong being slidable on a gas supply rail or conduit or manifold part of the cannula (herein called a manifold part) between an open and a closed configuration. In the open configuration the prong is moved along the manifold part to be aligned with a user's nare in use, and be in fluid communication with the manifold part of the cannula via an aperture in the manifold part. In a closed configuration the prong is moved along the manifold so that the prong is not in fluid communication with the manifold part, the being out of alignment from the aperture of the manifold.

The cannula may comprise a stop to limit the amount of movement of the prong.

The slidable prong may comprise a prong portion to be inserted into a nare of the user, and a base portion adapted to receive the manifold part to slide thereon.

The base portion of the sliding prong may extend laterally from the prong portion to cover an aperture in the manifold.

The cannula may comprise a collapsible or crushable or squashable prong or portion including a prong. The collapsible or crushable or squashable prong may be squashed, collapsed or crushed to block flow from that prong.

The cannula may comprise a foldable prong and a retaining member to retain the foldable prong in a folded position. In the folded position the prong is blocked or pinched off to prevent flow through the folded prong, and is clear of the user's nare to allow access for an instrument to be inserted.

Both prongs may be foldable.

The cannula may comprise two retaining members, each member corresponding with one folding prong.

The cannula may comprises a tearable manifold part.

The manifold part may be tearable at a section located in between the left and right nasal prongs. The torn section may be self sealing so that 100% of the flow is directed via the single prong into one nare of the user when one half is torn from the cannula.

The cannula may comprise a first side comprising a first prong and an inlet for receiving a flow of gas, and a second side comprising a second prong, wherein the first and second sides are separable. When the first and second sides are connected together, the second prong is in fluid communication with the inlet.

The first side may comprise a valve or aperture that seals on itself, so that when the second side is separated from the first side the flow from the inlet passes through the first prong, without flow through the aperture or valve.

Attachment of the second side to the first side may force or hold the valve open so that the inlet communicates with the second prong.

The cannula may comprise a sealable aperture for inserting an instrument through the cannula.

The aperture may be provided in a manifold part of the cannula in alignment with a nasal prong.

The cannula may comprise a valve, wherein the valve may be actuated from open to close by inserting an instrument through the cannula to prevent flow to the prong that receives the instrument.

One or both prongs may be configured to be torn from a manifold part of the cannula, wherein the action of tearing a prong from the cannula acts to seal or close the manifold of the cannula so that there is no opening or outlet from where the prong is torn.

The cannula may comprise two respiratory gas supply conduits, one conduit per side of the cannula, and wherein left and right sides of the cannula may be releasably connectable, and the left and right sides may not be in fluid communication when connected together. The left or right side may comprise a retaining member to hold the side of the cannula in a folded position to block flow from the corresponding supply conduit.

In accordance with at least one of the embodiments disclosed herein, a cannula comprises an extendable region or expandable region positioned between a left prong and a right prong of the cannula. The expandable region may comprise corrugations or concertina type sections. In some configurations, the expandable region of the cannula may be formed from an elastic material to stretch between an extended position and a non-extended position.

The cannula may be adapted to be used together with a dermal patch to hold the cannula in the extended position.

The cannula may comprise a frame that defines an extended position and a retracted position.

In accordance with at least one of the embodiments disclosed herein, a cannula or face mask may be adapted to interface with an airway instrument, for example a scope or diagnostics instrument, or an airway tube or conduit.

The cannula may comprise a guiding channel in an outer surface of the nasal prong.

The cannula may comprise a guiding channel in an inner surface of a nasal prong. For example, a nasal prong may be a multi-lumen nasal prong, wherein a lumen provides for a gas flow and another lumen provides for insertion of an instrument.

The guiding channel may extend along the length of one or both nasal prongs.

The guiding channel may extend laterally across the prong.

A face mask may comprise guiding channels for guiding instruments into the airway of a patient, the channels may be provided at an inside of the mask. The guiding channels may be open channels or fully closed channels. The mask may comprise one or more channels for guiding an instrument into the user's mouth, and one or more channels for guiding an instrument into the user's nose.

An inside of the mask is coated with material to allow condensate to drain down surface, or has micro-channels in an internal surface of the mask to help condensate drain down.

In accordance with at least one of the embodiments disclosed herein, a patient interface comprising a port for receiving an instrument to extend through the patient interface and into a patient's airway.

The port may be located on a manifold part of the interface.

The port may be located upon a nasal prong or upon each of a pair of nasal prongs of the interface.

The interface or the port, or both, may further comprise a shaped or otherwise moulded region suitable for accepting or receiving or locating or seating of the instrument relative to the interface or the port or both.

The port may comprises a closable (or re-closable) opening.

The port may comprise of a self-closing seal.

The port may further comprise of an instrument director.

The director may provide for a pre-determined geometry of the port to direct, locate or portion the instrument at a desired angle or orientation relative to the port.

The port may include a relatively rigid component to support an instrument upon insertion or entrance to the port.

The relatively more rigid component may provide a surface for positive orientation or definition of a secure location or seating position for an instrument.

The relatively more rigid component may provide for a pre-determined angle of insertion by the instrument to the port.

The port may comprises of a relatively softer or more flexible or compressible component that seals over the port.

The port may comprise a covering of a relatively elastic or elasticated cover material that stretches when the instrument is inserted and allows extension, optionally a seal is said elastic or elasticated cover material.

The port may be formed of a combination of a relatively more rigid component and a covering material of at least one layer of a relatively compressible material.

The port may allow for insertion of a relatively long instrument.

The port may direct the instrument along a prong of the interface.

The port may be located on a nasal prong of the interface.

In accordance with at least one of the embodiments disclosed herein, a cannula comprises a bite-block, the bite-block including an opening through which instruments may be provided into the patient's mouth.

In accordance with at least one of the embodiments disclosed herein, a nasal cannula comprises a manifold for receiving a gas flow, and a pair of prongs extending from the manifold to deliver a gas flow to a patient via the nares, wherein at least one prong is shaped or configured to i) reduce the amount of gas flow delivered to a corresponding nare as compared to the amount of gas flow delivered by the other prong to the other nare, and/or ii) allow an airway instrument to be inserted into a corresponding nare. The nasal cannula may be configured as described in any one or more of the above statements relating to cannulas comprising two nasal prongs.

According to those various embodiments and configurations described herein, a flow rate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100 L/min, about 70 to 80 L/min). Flowrates above about 15 L/min in some embodiments may be used in such configurations or embodiments, in particular but not limited to flowrates of about 60-70 L/min. 'High flow therapy' may refer to the delivery of gases to a patient at a flow rate of between about 5 or 10 L/min and about 100 L/min, or between about 15 L/min and about 95 L/min, or between about 20 L/min and about 90 L/min, or between about 25 L/min and about 85 L/min, or between about 30 L/min and about 80 L/min, or between about 35 L/min and about 75 L/min, or between about 40 L/min and about 70 L/min, or between about 45 L/min and about 65 L/min, or between about 50 L/min and about 60 L/min.

According to various configurations and embodiments described herein, there may be provided a use of a flowrate of gases supplied or provided to an interface or via a system for the introduction or delivery of a medicament into a user's airway, for example, but not limited to, a user's upper or lower airway.

According to various configurations and embodiments, there may be provided a therapy and/or a mechanism for using such relatively high flowrates to effectively drive or push medicament into the airway of a user. This may be due to the relatively high amount of force applied by such relatively high flowrates.

In various configurations or embodiments, the gases supplied to a user when provided at the flowrates above may provide for a jetting of the gas flow to carry or entrain medicament or particles or medicament further or deeper into the airway of the user than other traditional methodology of delivering medicament or when a user is under normal self-driven respiratory conditions.

Each of the various configurations or embodiments or configurations described herein may be utilised in combination with one or more of the other various systems, devices (including interfaces) or methods also described herein.

BRIEF DESCRIPTION OF THE DRAWINGS

Specific embodiments and modifications thereof will become apparent to those skilled in the art from the detailed description herein having reference to the figures that follow, of which:

FIG. 20 illustrates a face mask with channels for accommodating instruments.

FIG. 21 illustrates a respiratory gas conduit comprising instrument conduits in a wall of the gas conduit.

FIG. 22 illustrates a cannula comprising a bite-block.

DETAILED DESCRIPTION

In some instances it may be desirable to deliver a flow of respiratory gases to a patient via one or both nares and allow for the insertion of airway instruments or devices, for example a tube, via one of the nares. In some instances it may be desirable to allow an instrument to be inserted via a nare of a user and optionally, to block flow to that nare of the user, or to block flow to both nares or stop flow completely.

Figure 1A:
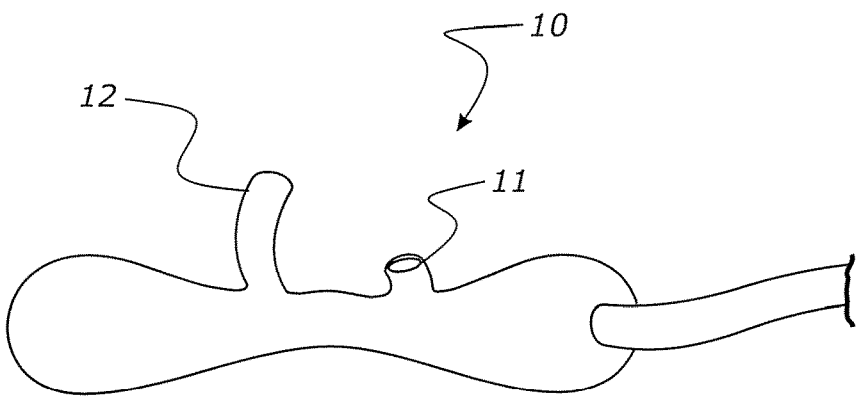
FIG. 1A illustrates a cannula with unequal length nasal prongs.

In some embodiments, a nasal cannula may comprise an asymmetric profile to reduce the size of the cannula under or near one nare of a user. For example, with reference to FIG. 1A, in some configurations, a nasal cannula 10 comprises two nasal prongs 11, 12, wherein one of the nasal prongs 11 is shorter than the other nasal prong 12. The shorter nasal prong may have a relatively minimal or substantially no extension into the nare of the patient. This arrangement provides room or space around the shorter prong for a nasal instrument to be inserted into the patient's nare. In some configurations, the cannula may comprise two prongs, wherein each prong is of a length to have relatively minimal or substantially no extension into the nares of the patient, so that an instrument may be inserted into either nare.

A cannula typically comprises a frame or manifold part. A conduit or interface tube may be attached to the frame or manifold part. The frame or manifold part supports the nasal prongs in a spaced apart relation for fitment into the patient's nares. The frame may optionally include a pair of rigid or semi rigid arms that extend across the cheeks to locate the cannula on the face. The arms may comprise an overmolded thermoplastic or other suitable material. The cannula may comprise a headgear to secure the cannula in an operational position on the user's head. In some configurations the nasal cannula may comprise a securement structure. A system for the securement of such a patient interface (e.g. nasal cannula) to the face can allow for a removable or connectable arrangement. For example, a securement structure or system may comprise a series of patches or pads, for connection to a user's face, and then one or more additional pads or patches for connection to the interface, the exposed surfaces of these pads or patches being provided with capability to connect or attach, preferably in a removable manner, to the other patches or pads. With reference to FIGS. 1B to 1E, in some embodiments the frame 21 or manifold part 21 of the cannula 20 is asymmetrical so that the frame or manifold is reduced in size on one side 21a compared to the other side 21b. The asymmetrical frame or manifold provides a cannula with an asymmetric profile to provide space at one nare for an instrument to enter that nare. For example, with reference to FIG. 1B, in some configurations the frame or manifold 21 tapers in size from one side or from one nasal prong 11, to the other side or other nasal prong 12. In some embodiments, the frame or manifold part may be asymmetric when viewed from the front. In some embodiments, the frame or manifold part may be asymmetric when viewed in plan view. Plan view and front view are used with reference to the cannula in place on a user and with the user in a standing or upright position. As shown in FIGS. 1B to 1E, in some embodiments, the frame or manifold part may be asymmetric when viewed from the front of the cannula and also when viewed in plan view. The side of the cannula that is reduced in size allows for an instrument to be inserted alongside the cannula and into the nare of a user that is adjacent the reduced side of the cannula. The frame or manifold part has a thickness extending between a backside of the cannula that locates against or adjacent the user's face below the user's nose and an opposite outwards front side of the cannula, and a height extending between a top of the frame or manifold part and a bottom of the frame or manifold part. Preferably the prongs extend from the top of the frame. As shown in FIG. 1D, the height of the frame or manifold part adjacent one nare of the user may be less than the height adjacent the other nare of the user. Additionally or alternatively the thickness of the frame or manifold part adjacent one nare of the user may be less than the thickness adjacent the other nare of the user.

Figure 1B:
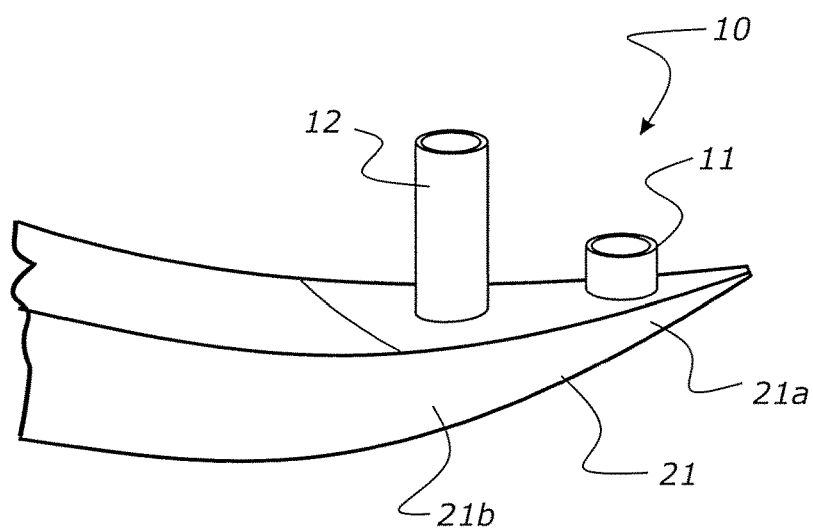
FIG. 1B illustrates an asymmetric cannula, wherein one side of the cannula is reduced in size.
Figure 1C:
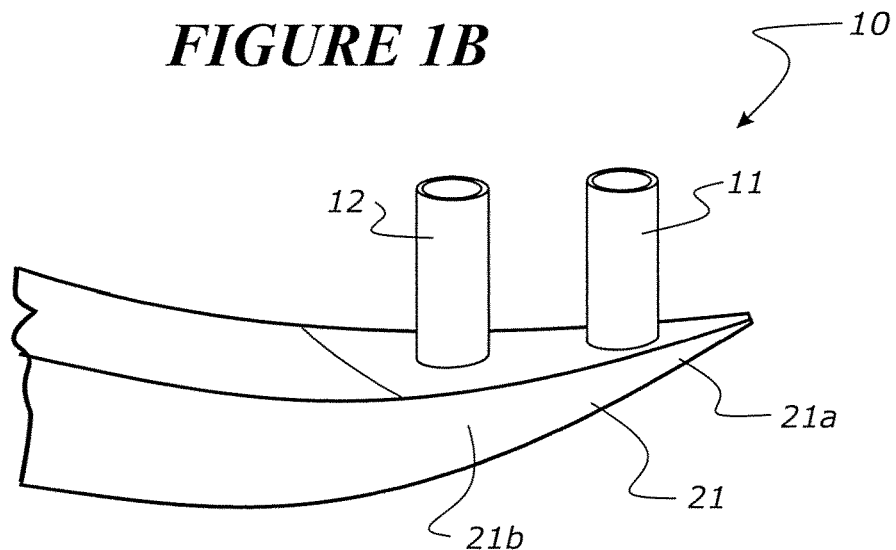
FIG. 1C illustrates another asymmetric cannula, wherein one side of the cannula is reduced in size.
Figure 1D:
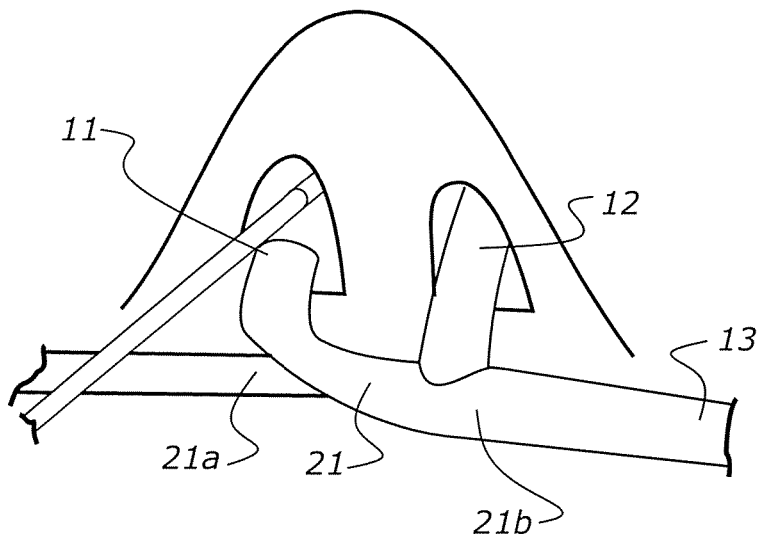
FIG. 1D is a front view of another asymmetrical cannula.

In some embodiments the prong on the reduced in size side of the cannula may be shorter in length than the other nasal prong (for example as shown in FIG. 1B), or cannula may comprise a prong-less nasal outlet on the 'reduced in size' side of the cannula. Alternatively, in some embodiments the prongs are of equal or similar length (FIG. 1C), or the prong on the 'reduced in size' side of the cannula may be longer than the other prong.

Figure 1E:
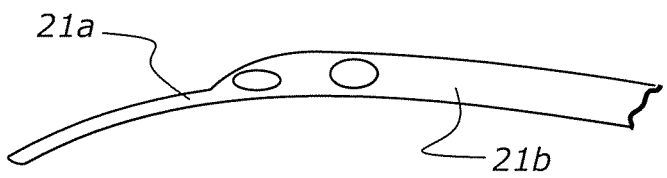
FIG. 1E is a plan view of the cannula of FIG. 1D.

In some configurations the nasal prong 11 at the 'reduced in size' side of the cannula may have an oval cross section or a shape that is flatter than a circle (for example as shown in FIG. 1E) to provide a space between the prong and the user's nare for an instrument to be inserted. FIG. 1D illustrates an instrument inserted into the nare on the side of the cannula that is reduced in size. In some configurations the nasal prong 11 at the 'reduced in size' side of the cannula may be shorter than the other prong 12, or the prongs may be of equal length.

An example of where a cannula comprising an asymmetric profile may be particularly useful is in suspended laryngoscopy. Equipment associated with the suspended laryngoscope is placed very close under the patient's nares and in some cases a prior art high flow cannula cannot be used as the cannula is too large to fit in place under the laryngoscope.

A gases supply tube or conduit may be connected to the cannula, or the cannula may comprise a conduit connection for connecting a supply tube or conduit. In some embodiments, the supply conduit or conduit connection may be provided to a side of the cannula opposite to the reduced side of the cannula, as shown in FIGS. 1B to 1E. This arrangement of the conduit away from the reduced side of the cannula further assists in maximizing space for an airway instrument or other device to be provided to the user's nare.

Unless otherwise indicated, one side of the cannula is intended to mean the portion of a cannula that is located on one side of a user's face in use (e.g. a left hand side of a user's face). An opposite side of the cannula is the portion of the cannula that is located on the other side of a user's face in use (e.g. a right hand side of a user's face). The terms "left" and "right" are intended to relate to the left hand side and right hand side of the user or patient.

Figure 2:
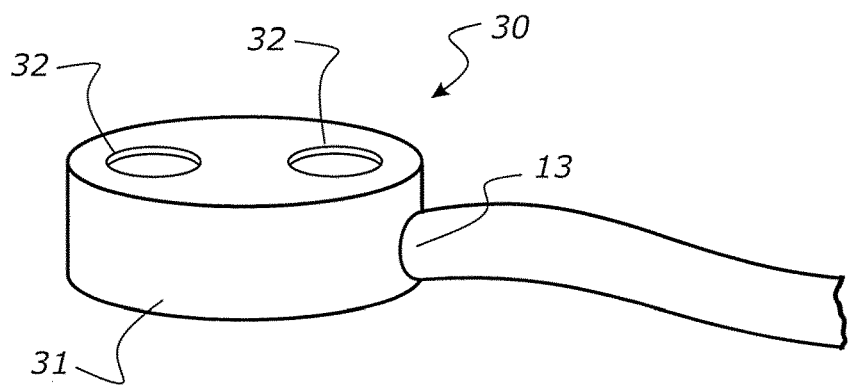
FIG. 2 illustrates a cannula without nasal prongs.

In some embodiments, as illustrated in FIG. 2, a cannula 30 does not have a nasal prong. Such a cannula comprises a manifold part or frame 31 that receives a flow of gases and redistributes that flow to each nare of a user via two outlets or apertures 32, each outlet corresponding with (or configured to communicate with) a nare of the user.

The embodiments described above may be useful as they may not require any adjustment of the cannula on the user's face in order to insert an instrument into a nare of the user, yet a flow of gases is still delivered to both nares.

In some configurations a 'frame' of a cannula may comprise a strap or may be a strap for securing the cannula in place on a patient's face in use.

Figure 3A:
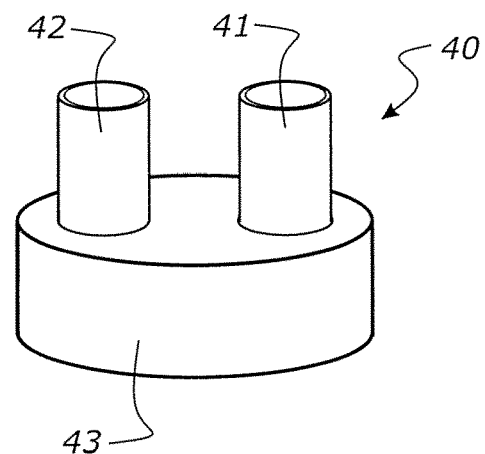
FIGS. 3A and 3B illustrate a cannula with a sliding nasal prong that may be moved between a retracted position and an extended position.
Figure 3B:
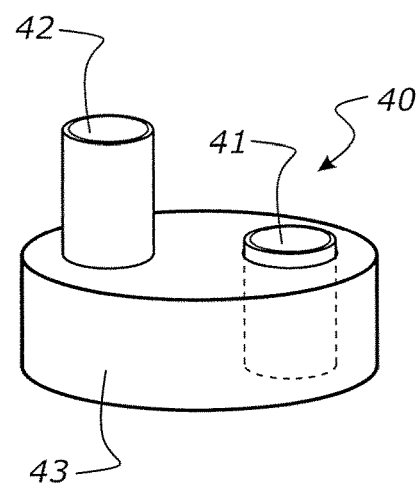

In some configurations a nasal cannula comprises a removable or extendable prong. For example, with reference to FIGS. 3A and 3B, at least one prong 41 is retractable into or extendable from a manifold 43 of the cannula 40. In FIG. 3A an extendable prong 41 is in an extended position, and in FIG. 3B the prong is retracted into the manifold 43. For example, the prong slides into and out of the manifold of the cannula. One or both prongs 41, 42 may be configured to be extendable, for example both prongs may slide into and out of the manifold of the cannula.

Figure 4A:
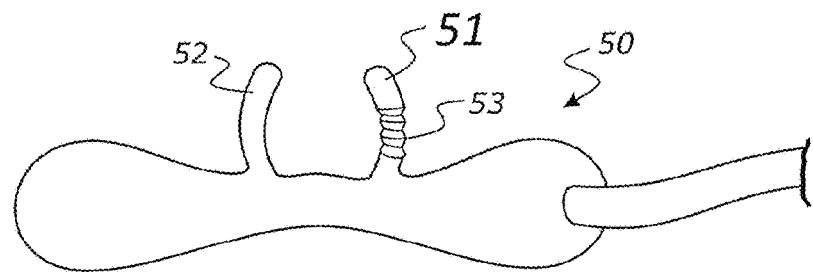
FIGS. 4A and 4B illustrate a cannula with an extendable nasal prong.
Figure 4B:
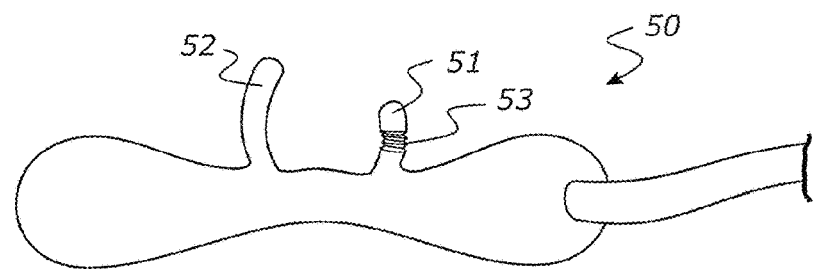

As illustrated in FIGS. 4A and 4B, in some configurations one or both prongs 51, 52 of the cannula 50 comprises corrugations or concertina type sections 53 which can be extended by a user to lengthen to extend the length of the prong, as shown in FIG. 4A. The corrugations may be formed at a base of the prong, or partway or fully along the length of the prong. To avoid clashing with an airway instrument the prong may be configured to a retracted position, as shown in FIG. 4B.

Figure 5:
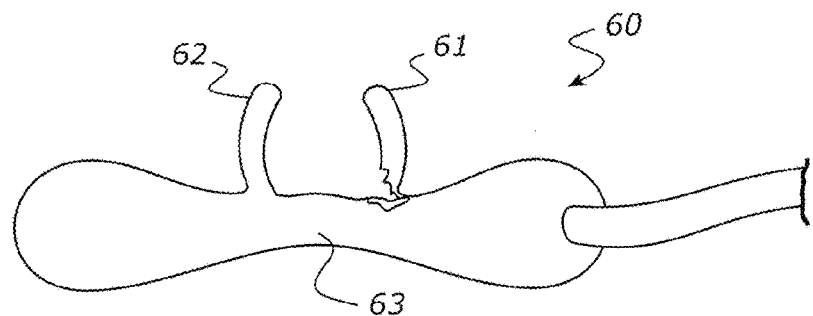
FIG. 5 illustrates a cannula with a tearable prong.
Figure 13:
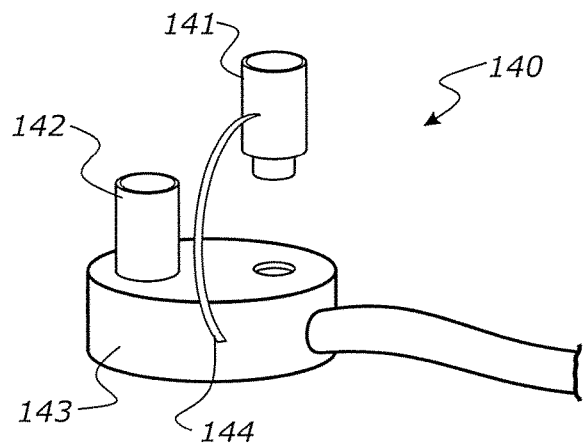
FIG. 13 illustrates a cannula with a removable prong.

As illustrated in FIG. 5, in some configurations one or both prongs 61, 62 may be configured to be torn from a manifold part 63 of the cannula 60. To create space for an instrument to be inserted into a nare of the user, one prong may be torn from the cannula, to leave an opening or outlet for gases to flow to the corresponding nare of the user. Alternatively, in some configurations, for example as shown in FIG. 13, one or both nasal prongs 141, 142 may be removably attached to a manifold part 143 of the cannula 140. To create space for an instrument to be inserted into a nare of the user, one prong 141 may be releasably detached from the cannula 140. The prong may be releasably reattached for future use. The releasable prong may be permanently attached to the cannula assembly, for example by a lanyard or leash 144.

Figure 6:
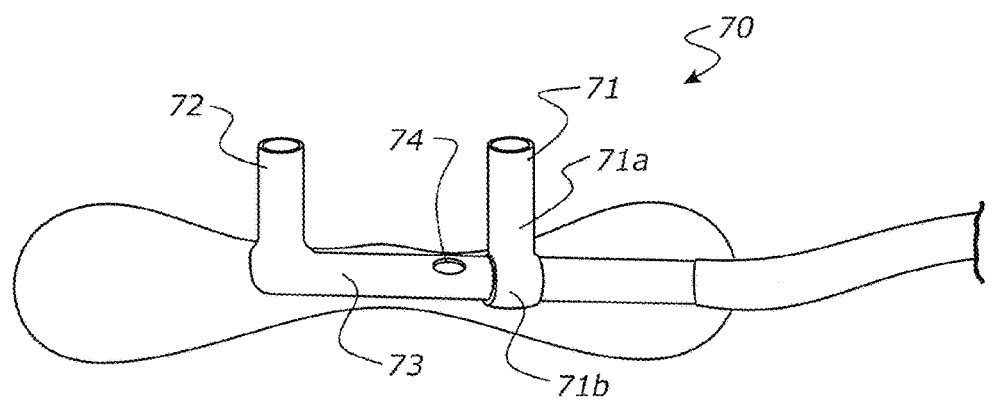
FIG. 6 illustrates a cannula with a slidable prong to expose an aperture to provide flow to a nare of patient via the aperture rather than by the slidable prong.

As illustrated in FIG. 6, in some configurations one or both prongs 71, 72 may be slidable or rotatable relative to the other prong or to a manifold part 73 of the cannula, to displace the prong from a user's nare in use to provide access for an instrument to be inserted into the nare left vacant by sliding the prong. For example, as illustrated in FIG. 6, in some configurations a nasal cannula may comprise a gas supply rail or conduit (manifold part) 73, and one prong 71 may be slidable on the rail or supply conduit 73. The slidable prong may comprise a prong portion 71a to be inserted into a nare of the user, and a base portion 71b adapted to receive the manifold part to slide thereon. Where the prong is slid out of alignment with a user's nare, an orifice or aperture 74 in a wall of the rail or conduit is exposed and may provide some gas flow from the rail or conduit to the exposed nare of the user. With the prong slid out of alignment with the user's nare, space is created to allow an instrument to be inserted into the exposed nare. In some embodiments both prongs 71, 72 may be slidable on a rail or supply conduit or manifold of the cannula.

The embodiments described with reference to FIGS. 3A to 6 and FIG. 13 maintain delivery of respiratory gas flow to both nares, while providing a cannula that is flexible in terms of treatment options, for example:

Change may be temporary and respiratory support can be restored when instrument/device is not in use.

Change can be achieved easily and without removing interface.

As flow through both nares is maintained some flow may be able to enter the nare around instrument/device. This may help to keep the nare/airway patent and also allow minimal change in respiratory support.

Flow through one nare may be maintained by one prong as flow and delivered pressure to that nare does not change. This may avoid higher velocity jets that may damage nasal tissue, as is the case where all flow is redirected to one nare.

Allowing the flow to continue to flow through both orifices may prevent large pressure changes in the system. If the gas supply is sensitive to pressure changes (e.g. a blower) this may also help to reduce potential fluctuations in flow and/or humidity, or a reduction in flow if the supply is not able to overcome the increase in pressure.

Figure 7:
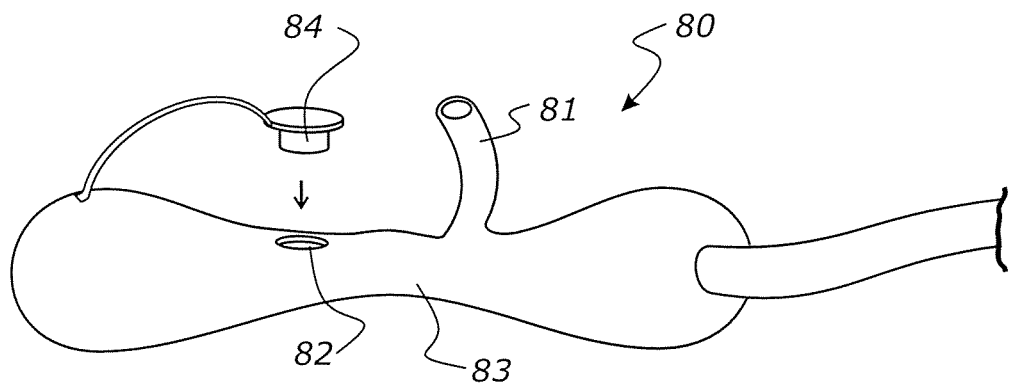
FIG. 7 illustrates a cannula with an opening that may be closed by a cap.

As illustrated in FIG. 7, in some configurations flow to one nare may be optional, while flow to the other nare may be permanently provided. In the embodiment of FIG. 7, the cannula 80 comprises one nasal prong 81 to provide a flow of gas to a nare of a user, and an opening or aperture 82 in a manifold 83 of the nasal cannula that may be capped or plugged by a cap 84. Flow to one nare is provided optionally by capping or uncapping the opening. In an alternative embodiment the nasal cannula may comprise a pair of outlets, wherein the outlets are prong-less.

Figure 8A:
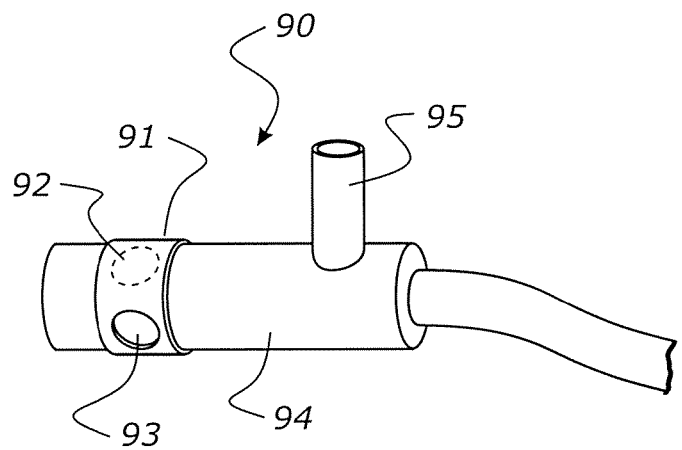
FIGS. 8A and 8B illustrate a cannula with a rotating cuff to open and close an aperture for providing flow to a nare of a patient.
Figure 8B:
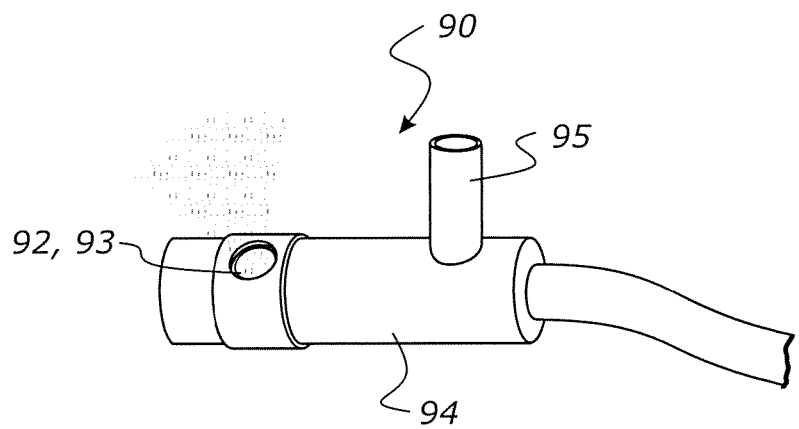

As shown in FIGS. 8A and 8B, in some embodiments a cannula 90 may comprise a rotatable cuff 91 to block or unblock an opening or aperture 92 on a manifold 94 of the cannula to optionally provide a flow of gas to one nare of the user. The rotatable cuff has an aperture 93 to align with the manifold aperture 92 to allow flow from the manifold aperture 92 to the user's nare. The nasal prong 95 maintains flow permanently to the other nare. FIG. 8A shows the cuff 91 rotated to block the opening 92 and prevent flow to one nare, and FIG. 8B shows the cuff 91 rotated to unblock the opening 92 by aligning the cuff aperture 93 with the manifold aperture 92 and allow flow to the nare. The blocking of one outlet may assist a clinician to insert a nasal instrument into the nare that corresponds with the occluded outlet.

The embodiments described with reference to FIGS. 7 and 8A/8B maintain delivery of respiratory gas flow to at least one nare, while providing a cannula that is flexible in terms of treatment options, for example:

The user can optionally block the flow to one of the nares. The change may be temporary.

The change can be achieved easily and without removing the interface.

A prong is absent from one nare allowing instruments to be inserted at all times without having to alter the interface.

The choice of providing flow to the nare causes minimal interference with the nare; even if flow is provided through the opening, there is reduced or no physical obstruction to an instrument inserted into the nare.

Where flow is permitted through the opening (i.e. flow is delivered to both nares), some flow may be able to enter the nare around the instrument/device. This may help to keep the nare/airway patent and also allow minimal change in respiratory support.

If the opening is blocked, flow may be redirected to the main prong, maintaining total flow delivered to the patient and pressure delivered to the lower airway.

The ability to block the opening/gas flow means lightweight or sensitive instruments can be used without gas flow interfering with alignment.

Figure 9:
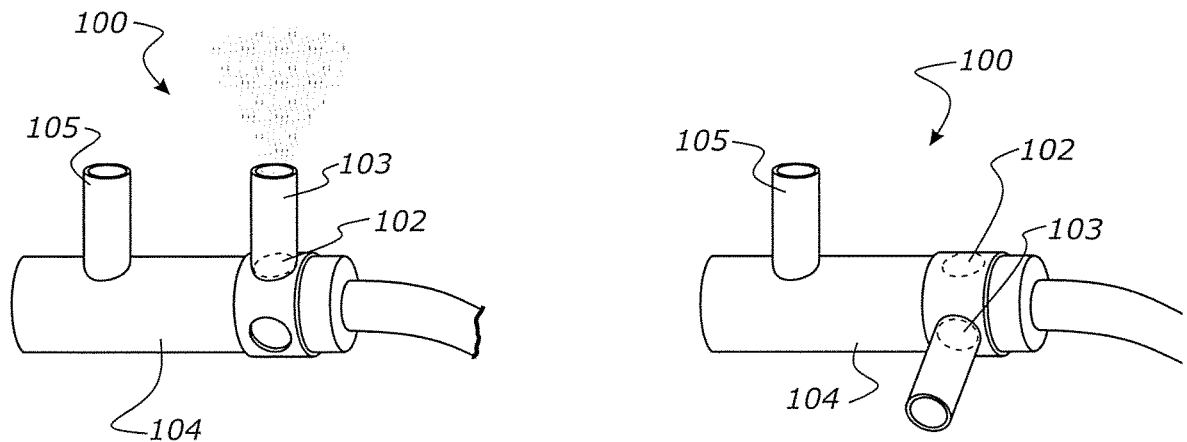
FIG. 9 illustrates a cannula with a rotating prong.

With reference to FIGS. 9 to 16B, in some configurations flow to one nare may be optionally provided via a nasal prong. Flow to the other nare may be permanently provided via a nasal prong. As shown in FIG. 9, in some configurations a nasal cannula 100 comprises a rotatable prong 101. One or both prongs may be rotatable. The prong may be rotatable on a gas supply rail or conduit or manifold 104 part of the cannula (herein called a manifold part). In an open configuration the prong 103 is rotated to be aligned with a user's nare in use, and be in fluid communication with the manifold part of the cannula via an aperture 102 in the manifold part. In a closed configuration the prong 103 is rotated, for example rotated forward from the user's face, so that the prong is not in fluid communication with the manifold part as the prong is rotated out of alignment from the aperture of the manifold. In the closed position the prong is moved out of alignment with the user's nare to provide access into the nare for an instrument to be inserted. In the closed configuration, 100% of the flow is directed via the single prong into one nare of the user. In some embodiments both prongs 103, 105 may be rotatable on a rail or supply conduit or manifold of the cannula, so that a user may choose which prong to rotate and which nare to insert an instrument.

Figure 10:
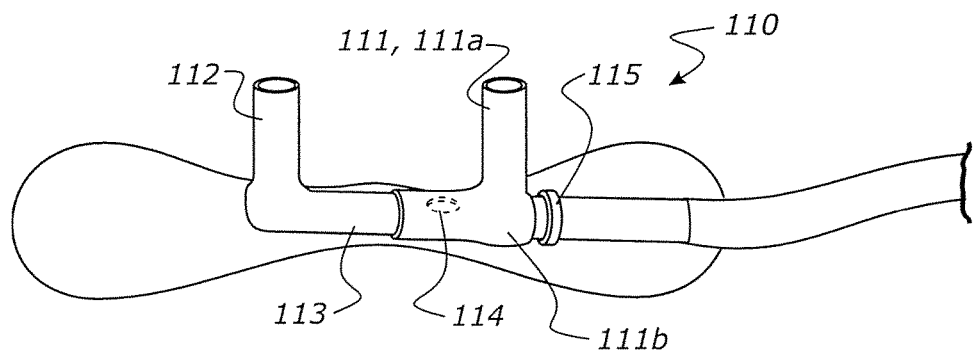
FIG. 10 illustrates another cannula comprising a sliding nasal prong.

As shown in FIG. 10, in some configurations a nasal cannula 110 comprises a slidable prong 111. The prong 111 is slidable on a gas supply rail or conduit or manifold part 113 of the cannula (herein called a manifold part). In an open configuration the prong is moved along the manifold part to be aligned with a user's nare in use, and be in fluid communication with the manifold part of the cannula via an aperture 114 in the manifold part. In a closed configuration the prong is moved along the manifold so that the prong is not in fluid communication with the manifold part as the prong is moved out of alignment from the aperture of the manifold, as shown in FIG. 10. In the closed position the prong is moved out of alignment with the user's nare to provide access into the nare for an instrument to be inserted. In the closed configuration, 100% of the flow is directed via the single prong into one nare of the user. Movement of the prong in one direction along the manifold part may be limited by a stop 115, to prevent the aperture 114 in the manifold becoming uncovered. Movement of the prong in an opposite direction along the manifold part may be limited by a stop or by the other prong 112, to set the alignment of the sliding prong with the aperture. The slidable prong 111 may comprise a prong portion 111a, to be inserted into a nare of the user, and a base portion 111b adapted to receive the manifold part to slide thereon. The embodiment of FIG. 10 is similar to the embodiment of FIG. 6, however in FIG. 10 the base portion 111b of the sliding prong 111 extends laterally from the prong portion 111a to cover the aperture 114 so that the aperture is blocked by the base portion when the prong portion is not aligned with the aperture. In some embodiments both prongs are slidable prongs, each slidable on a manifold part of the cannula.

In some configurations, a cannula has a first prong attached to and in fluid communication with a first conduit part, and a second prong attached to and in fluid communication with a second conduit part, wherein the second conduit part is slidable relative to and in fluid communication with the first conduit part to displace the second prong from the first prong. In some embodiments, as illustrated, the second conduit part comprises an aperture in a side wall to align with the first prong when the second prong is positioned for alignment with a nare of the user, so that the first prong is in fluid communication with a flow of gases provided via an inlet of the cannula.

Figure 11A:
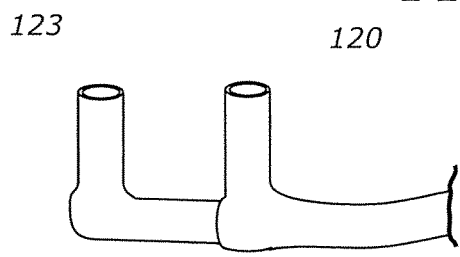
FIGS. 11A and 11B illustrate a cannula with a collapsible prong.
Figure 11B:
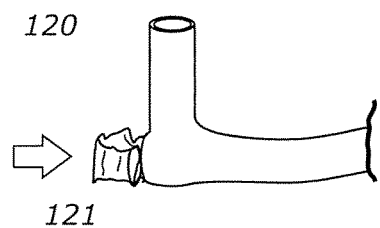

As shown in FIGS. 11A and 11B, in some configurations a cannula 120 may comprise a collapsible or crushable or squashable prong or portion including a prong. The collapsible or crushable or squashable prong 121 is squashed, collapsed or crushed to block flow from that prong. When the prong is squashed, collapsed or crushed it is clear of the user's nare to allow access for an instrument to be inserted. In some configurations both prongs may be collapsible or crushable or squashable.

Figure 12A:
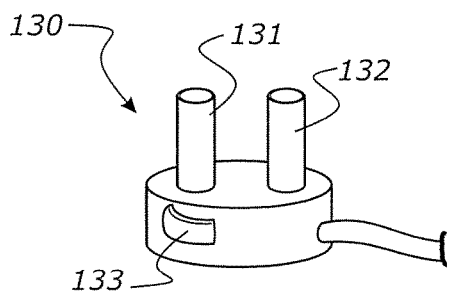
FIGS. 12A and 12B illustrate a cannula with a folding prong.
Figure 12B:
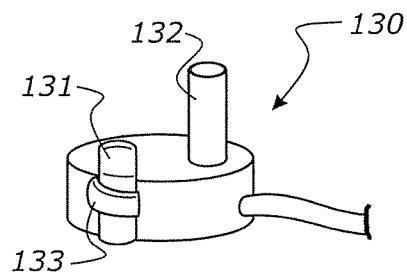

As shown in FIGS. 12A and 12B, in some configurations a cannula 130 comprises a foldable prong 131 and a retaining member 133 such as a clip to retain the foldable prong in a folded position. In the folded position the prong is blocked or pinched off to prevent flow through the folded prong, and is clear of the user's nare to allow access for an instrument to be inserted. In some configurations both prongs may be foldable. The cannula 130 may comprise two retaining members, each member corresponding with one folding prong.

Figure 14A:
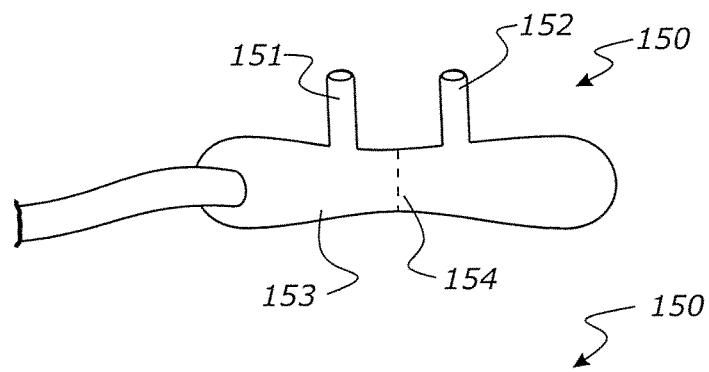
FIGS. 14A and 14B illustrate a cannula with a tearable portion or section to remove one half of the cannula.
Figure 14B:
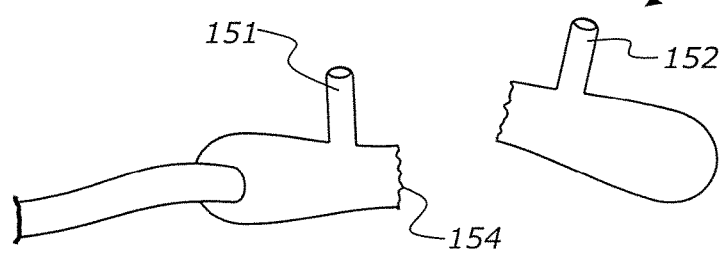

As shown in FIGS. 14A and 14B, in some configurations, a cannula 150 comprises a tearable manifold part 153. The manifold part is tearable at a section 154 located in between the left and right nasal prongs. The torn section may be self-sealing so that 100% of the flow is directed via the single prong into one nare of the user when one half is torn from the cannula.

Figure 15:
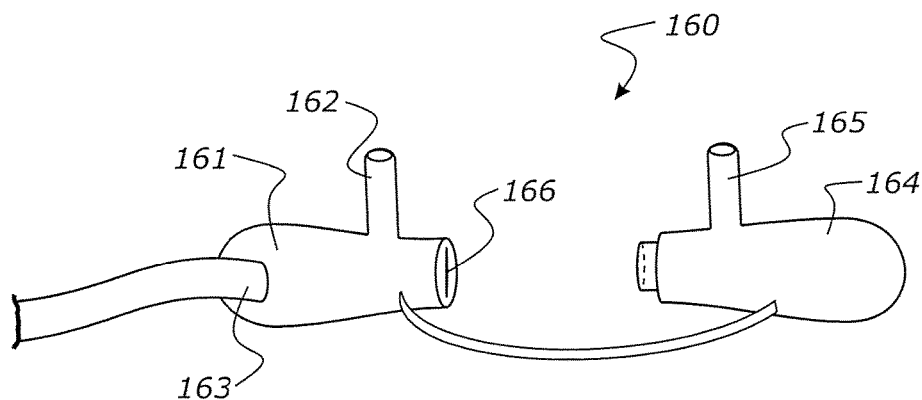
FIG. 15 illustrates a cannula with two sides that may be separated.

As shown in FIG. 15, in some configurations, a cannula 160 may comprise a first side 161 comprising a first prong 162 and an inlet 163 for receiving a flow of gas, and a second side 164 comprising a second prong 165, wherein the first and second sides are separable. The first prong is in fluid communication with the inlet. When the first and second sides are connected together, the second prong is in fluid communication with the inlet. The first side also may comprise a valve 166 or aperture 166 that seals on itself, so that when the second side is separated from the first side the flow from the inlet passes through the first prong, without flow through the aperture or valve. Attachment of the second side to the first side forces or holds the valve 166 open so that the inlet communicates with the second prong.

Figure 16A:
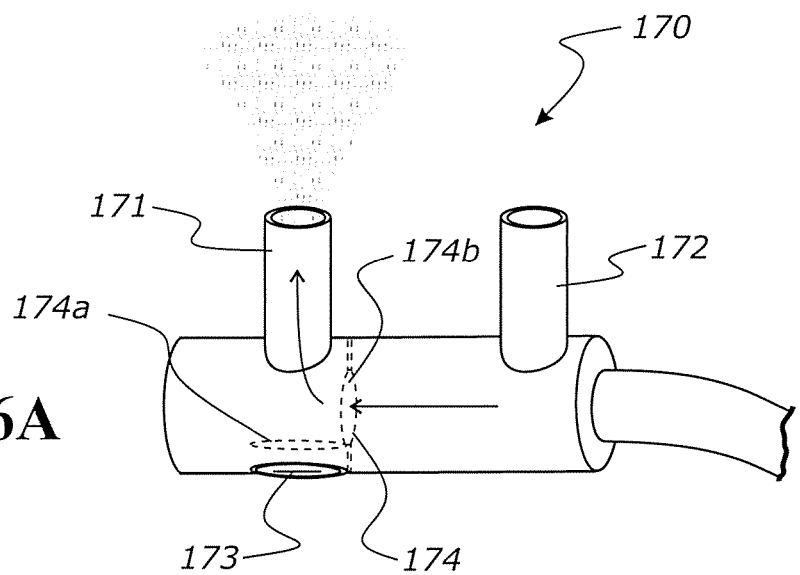
FIGS. 16A and 16B illustrate a cannula with a port for inserting an instrument along a prong of the cannula, and a one way valve for closing flow to the prong when an instrument is inserted.
Figure 16B:
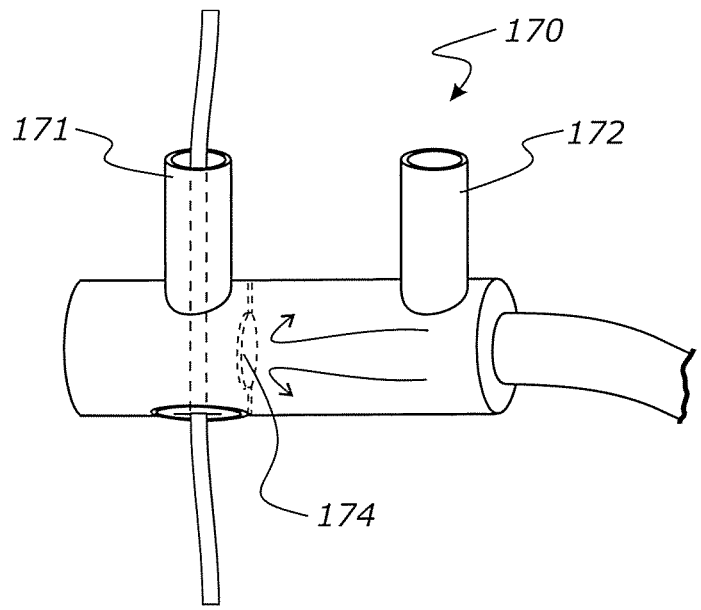

As shown in FIGS. 16A and 16B, in some configurations, a cannula 170 comprises a sealable aperture 173 (for example an aperture and a valve) for inserting an instrument through the cannula. The aperture 173 seals around an instrument when inserted into the aperture, and closes in a sealed configuration when the instrument is removed from the aperture. Such an aperture 173 may be provided to any one of the nasal cannulas described herein. The aperture may be provided in a manifold part of the cannula in alignment with a nasal prong so that an instrument may be inserted through the aperture and along the prong into a user's nasal passage. The aperture may also be provided in the manifold without being in alignment with a prong, such that the instrument may be inserted into the manifold without extending into or along the prong.

In some embodiments, the cannula comprises a valve 174. The valve may be actuated from open to closed by inserting an instrument through the cannula. The valve may be located within the manifold part of the cannula and between the prongs or outlets of the cannula. The valve is closed by the instrument extending through a second prong of the cannula so that gas flow from an inlet of the cannula is directed to a first prong of the cannula. When the instrument is inserted through the aperture the instrument actuates a valve element (e.g. a flap) against a valve seat to fluidly isolate one nasal prong or outlet from the other nasal prong or outlet and stop or reduce flow to the prong that receives the instrument. In some configurations, the cannula may comprise two sealable apertures, each aperture aligned with a corresponding prong. The cannula may comprise two valves, each valve corresponding with a prong. In such an embodiment, an instrument may be inserted simultaneously via both nares of the user. In some embodiments, the cannula may comprise a pressure relieve valve in the event that flow from both nasal prongs or nasal outlets is blocked.

In some configurations, one or both prongs may be configured to be torn from a manifold part of the cannula. However, unlike the configuration described with reference to FIG. 5, in some embodiments the action of tearing a prong from the cannula could act to seal or close off the flow conduit provided by the cannula so that there is no opening or outlet from where the prong is torn.

The nasal cannula configurations described with reference to FIGS. 9 to 16B allow for easier interfacing with a nasal instrument. Specifically the nasal instrument can be interfaced with the nasal cannula at the region of the prong that is modified or manipulated, for example by moving a prong out of the way of the user's nare as described. The cannulae therefore may be manipulated or modified so they interface with nasal instruments inserted into at least one nare while still being able to maintain high flow therapy delivery via the other nare. The embodiments described with reference to FIGS. 9 to 16B maintain delivery of respiratory gas flow to at least one nare, for example high flow delivery of respiratory gas, while providing a cannula that is flexible in terms of treatment options, for example:
  the user can optionally block the flow to one of the nares,
  change may be temporary,
  change can be achieved easily and without removing interface,
  can be configured so that flow or prong does not interfere with an instrument,
  when prong is oriented to be clear of the nare, flow is directed to the other prong, maintaining total flow and pressure delivered to the user.

Furthermore, in all embodiments, the arrangement described for modifying or manipulating one nasal prong may be applied for modifying or manipulating both nasal prongs, for example if access to both nares is desired. Where both nasal prongs or outlets can be blocked, a pressure relief valve may be provided to limit a maximum pressure that the system may be exposed to.

Figure 17A:
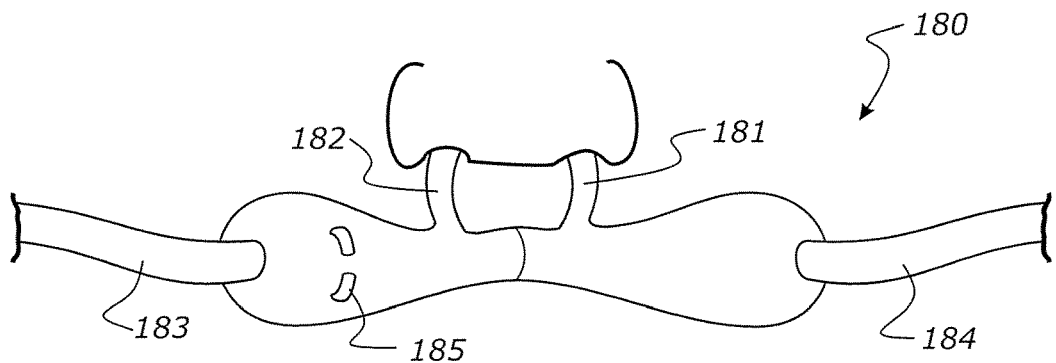
FIGS. 17A and 17B illustrate a cannula with two sides that may be separated.
Figure 17B:
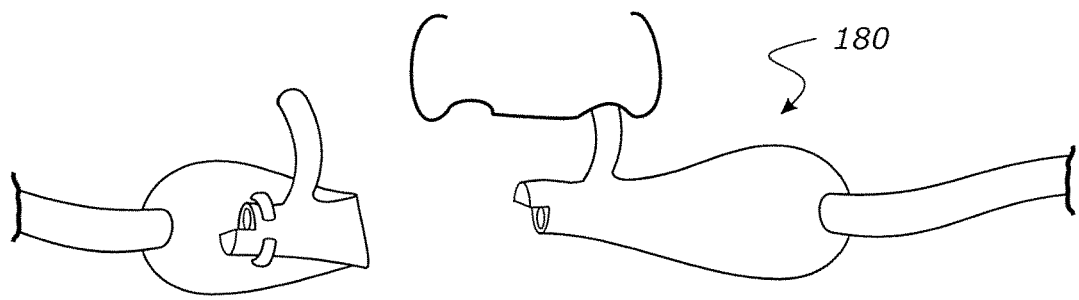

With reference to FIGS. 17A and 17B, in some configurations flow to the cannula 180 may be provided by two respiratory gas conduits 183, 184, one conduit per side of the cannula, or in other words each nasal prong 181, 182 has a dedicated gas supply. The left and right sides of the cannula may not be in fluid communication when coupled together as shown in FIG. 17A. In such embodiments, a left side and a right side of the cannula may be releasably connectable. Where insertion of an instrument is not required, the left and right sides of the cannula may be clipped or connected together and respiratory gas provided from the left and right nasal prongs to both nares of the user. Where an instrument is to be inserted, the left and right sides may be disconnected, and one of the sides used to provide the flow of gas via a nare of the user.

In some embodiments, the left and right sides of the cannula may be in fluid communication when coupled together as shown in FIG. 17A. Where an instrument is to be inserted, the left and right sides may be disconnected. The side of the cannula not in use may be placed away from the user's face, and may be folded to pinch the flow of gas to close off the flow of gas to the side of the cannula not being used. The side of the cannula not in use may be held in a folded position by a retaining member 185 or clip. Or the removed side may remain open and flow still allowed to flow, for example where a reduced flow to the patient is acceptable or if the instrument is to be inserted into the patient's nare for a short time period. Alternatively, the cannula may comprise a valve in each side of the cannula that is configured between an open state and a closed state by connecting and disconnecting the sides of the cannula. The valve may close when the sides of the cannula are disconnected. When an instrument is removed from the user's nare the two sides may be reconnected and gas supply via both nares may resume.

Figure 18A:
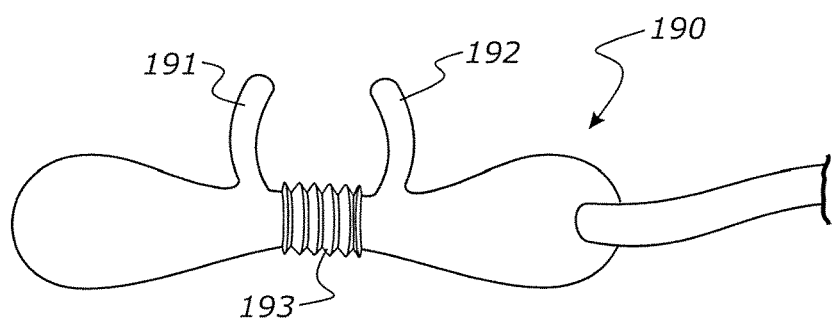
FIGS. 18A and 18B illustrate a cannula with an expandable section between a left and right nasal prong.
Figure 18B:
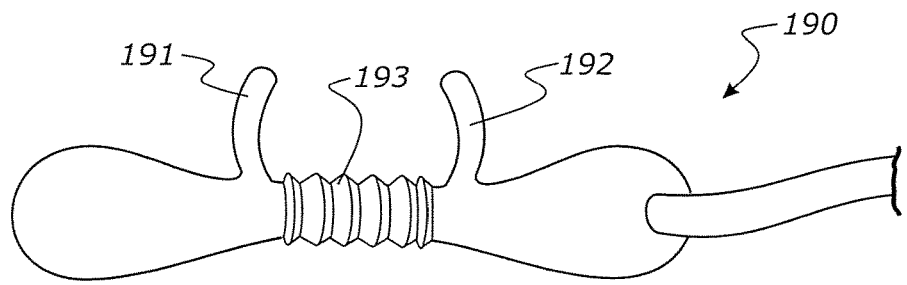

With reference to FIGS. 18A and 18B, in some configurations a cannula 190 comprises an extendable region or expandable region 193 positioned between a left prong 192 and a right prong 191 of the cannula. The expandable region may comprise corrugations or concertina type sections which can be extended by a user to lengthen or to extend the length of the prong, as shown in FIG. 18B. In use, where an instrument is to be inserted in a nare of the user, the expandable region may be expanded to an expanded or extended position as shown in FIG. 18B to vacate the user's nare. Where no instrument is required, the expandable region may be in the retracted or non-extended position as shown in FIG. 18A to provide a flow of gases to both nares of the user.

A cannula may be secured in place on a user's face by a dermal patch. A dermal patch may be adhered to a user's face, for example by a dermatologically sensitive adhesive. A second patch (interface patch) may be attached to a face side of a cannula. The dermal patch and the interface patch each have one half of a two-part releasable connection, for example one patch may have the hooks of a hook and loop connection and the other patch may have the loops of a hook and loop connection (for example the connection may be Velcro®). Thus the patches retain the cannula in position on the user's face. In some configurations, where a dermal patch is used to secure the cannula in place on the users face, the cannula 190 may be held in the extended position (FIG. 18B) or in the retracted position (FIG. 18A) by the dermal patch. Alternatively, the expandable region may be rigid enough to allow the extended side of the cannula to be disconnected from its dermal patch and be self-supported in the expanded position, or folded away from the patient's face.

In some configurations, the expandable region 193 of the cannula may be formed from an elastic material to stretch between an extended position and a non-extended position. In use, where no instrument is required, the expandable region may be in a non-stretched state so that both prongs interface with the nares of the user. Where an instrument is to be inserted, the expandable region formed from elastic material may be stretched to an extended position and held in the extended or stretched position by a dermal patch that is attached to the user's face. The cannula may be held in the stretched state by a dermal patch as described above. Alternatively, the cannula may comprise a frame that defines an extended position and a retracted position. For example, in the expanded condition (FIG. 18B) the cannula may be clipped to a frame to retain it in the expanded position.

The embodiments described with reference to FIGS. 17A to 18B maintain flow to one nare of the user, and is configurable to displace a prong away from the other nare of the user. Where a prong is displaced from the user's nare, gas flow to the cannula may not be directed to the other single prong, which may be advantageous in some circumstances as this arrangement may avoid a higher velocity jet of gas into the user's nare due to directing all flow to a single prong, like in embodiments of FIGS. 9 to 16B. The various embodiments allow for easier interfacing with a nasal instrument via the nare corresponding to the prong that is manipulated (e.g., moved or removed from the user's nare).

Figure 19A:
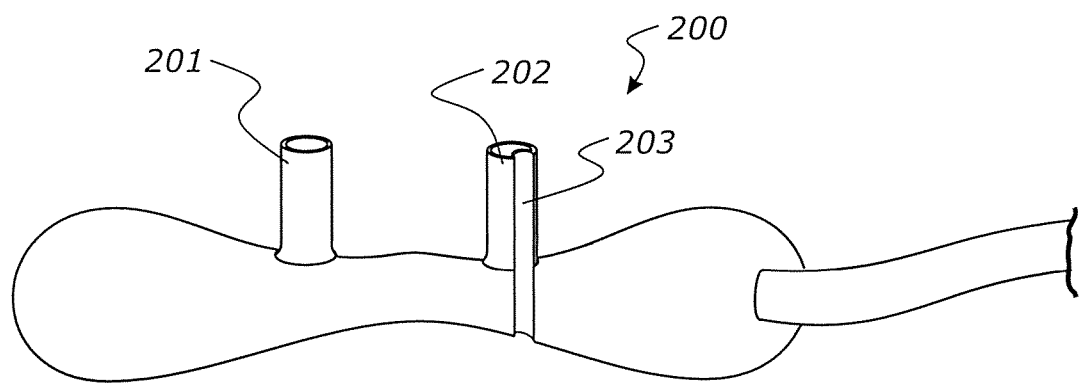
FIGS. 19A and 19B illustrates a cannula with a channel for accommodating an instrument.
Figure 19B:
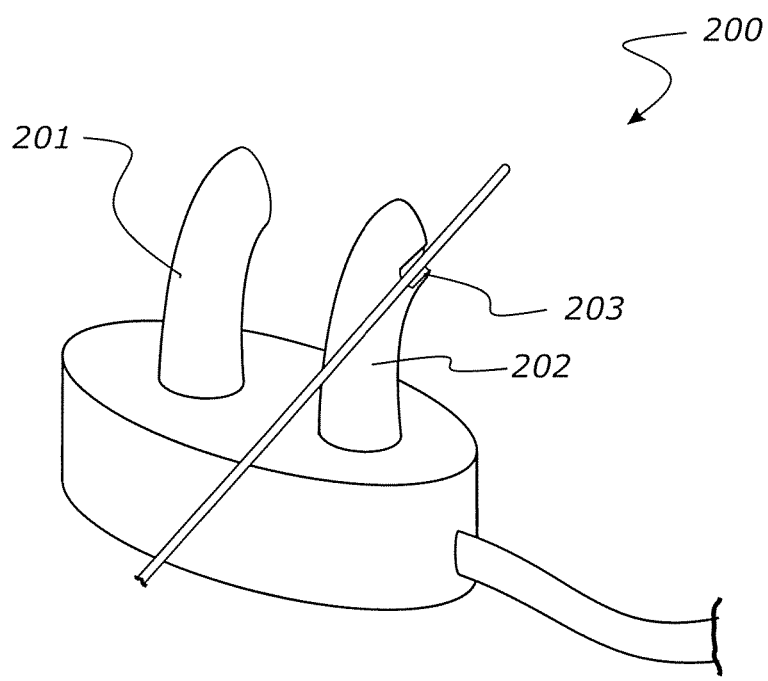

In some embodiments, a patient interface such as a cannula or face mask may be adapted to interface with an airway instrument, for example a scope or diagnostics instrument, or an airway tube or conduit. To interface with an airway instrument a cannula may comprise a guiding channel to receive and guide the instrument. For example, as illustrated in FIG. 19A, in some configurations, a cannula 200 may comprise a guiding channel 203 along the length of one or both nasal prongs 201, 202, and/or on a manifold of the cannula. As illustrated in FIG. 19B, in some embodiments a prong 202 may have a guiding channel 203 extending laterally across the prong. As shown in FIGS. 19A and 19B, in some embodiments the guiding channel is formed in an outer surface of the nasal prong. In some configurations, the guiding channel may be formed in an inner surface of a nasal prong. For example, a nasal prong may be a multi-lumen nasal prong, wherein a lumen provides for a gas flow and another lumen provides a port or conduit for insertion of an instrument. With multiple lumens the insertion of a device or instrument may not cause a large increase in back pressure as one lumen is dedicated to the passage of the device or instrument while another lumen provides a flow-path to the user's airway.

FIG. 20 illustrates a face mask 210 which includes guiding channels 211, 212 for guiding instruments into the airway of a patient provided at an inside of the mask. The guiding channels may be open channels (like 212), or fully closed channels (like 211). That is, in some configurations the guiding channel may be a tubing conduit along which the instrument may be threaded. In the embodiment of FIG. 20, the guiding channels are curved to guide flexible instruments into the patient's airway. A channel may be provided to guide an instrument into the user's mouth, and another channel to guide an instrument into the user's nose. An inside of the mask may be coated with material designed to allow condensate to drain down the surface. This would help a user see inside the mask to guide instruments. Alternatively the mask may have micro-channels in an internal surface of the mask to help condensate drain down.

A face mask (e.g. nasal mask or full face mask) includes a seal to seal against the face of a user. In some configurations, a face mask may have thinned portions in the seal on one side or on all sides. The thinned portions in the seal allow for a tube or other airway instrument to be inserted, and may allow for a seal to be created over the tube or instrument. The thinned portion of the seal may be more malleable and pliable and hence may conform to the shape of the tube while still maintaining a seal. The tube may be a nasogastric tube (NG or NT tube, e.g., a tube inserted through the nostrils).

Patient interfaces may have entry ports for instruments to be inserted through the interface and into a patient's airway. For example, as shown in FIG. 21, a nasal prong or other respiratory gas conduit 220 may comprise instrument ports or conduits 221 formed in a wall 222 of the prong or gas conduit, the instrument conduits extending longitudinally along the prong or gas conduit. The conduits 221 provide a lumen along which an instrument may be threaded to be guided into the patient's airway. A face mask may comprise two instrument ports, one for inserting an instrument to a patient's mouth, and a second port for inserting an instrument into the patient's nose. The ports may be closed by a valve, for example a duck billed valve, if necessary to prevent leaking of breathing gases via the port.

In some embodiments, as illustrated in FIG. 22, a cannula 240 may be provided with a 'bite-block' 241. The bite block is an item that is inserted into a patient's mouth and on which the patient may bite down but which holds the patient's mouth open. The block includes an opening through which instruments may be provided into the patient's mouth, and prevents a patient from biting an instrument.

The various embodiments described above may be particularly suitable for use with a range of instruments or airway instruments, including airway tubes or conduits, oral or nasal catheters, drug (medicament) delivery devices (eg: spray bottle, atomiser device, syringe), surgical instruments including spatulas, introducers/bougies, stylets, guides, tube exchangers, oral/nasal endotracheal tubes, nasopharyngeal airways (nasal trumpets), and scopes or diagnostics instruments such as laryngoscopes (direct or video) endoscopes, rigid or flexible bronchoscopes, esophagoscopes and fibreoptic scopes.

A patient interface 230, such as a nasal cannula, may comprise of a port 232 for delivery of a medicament into a flow F of a fluid (such as a gas) being delivered to a user and/or for interfacing with a medicament delivery device or an instrument. When a delivery device (dispenser) interfaces with a patient interface (e.g. nasal cannula) the dispenser may be used to dispense medicament into a flow path (e.g. a patient's airways) with or without a flow of fluid applied to the patient's airways via the cannula.

The medicament may optionally include one or more excipients, such as pharmaceutically acceptable excipients. Such a medicament may be those suitable for being administered to the airway of a user, whether as an atomised, nebulised or dispersed or other form suitable to be introduced into a flow of gas for administration and/or delivery to a user.

In some configurations, the port 232 may allow an instrument 1000 (e.g. a tube) or a medicament dispenser 234 (e.g. a spray bottle, atomiser device or syringe) to be insert thereto for dispensing of said medicament. For example, the port 232 may be located upon a manifold part 236 of the interface 230 such that dispensing of the medicament provides for dispersal into a relatively high flow rate of gas provided to the user, and which can carry the medicament into an airway of the user. For example, see FIG. 23A. Delivery of the medicament simultaneously with the delivery of high flow may help to deposit the medicament far down into the patient's airway (for example to the patient's vocal cords), reducing the chance of the medicament being deposited prematurely within the patient's airway (for example depositing in the patient's nasal cavity).

Other instruments that the port 232 may be adapted to interface with include airway tubes or conduits, introducers/bougies, stylets, guides, tube exchangers, and scopes or diagnostics instruments such as endoscopes, rigid or flexible bronchoscopes, esophagoscopes and fibreoptic scopes.

Figure 24A:
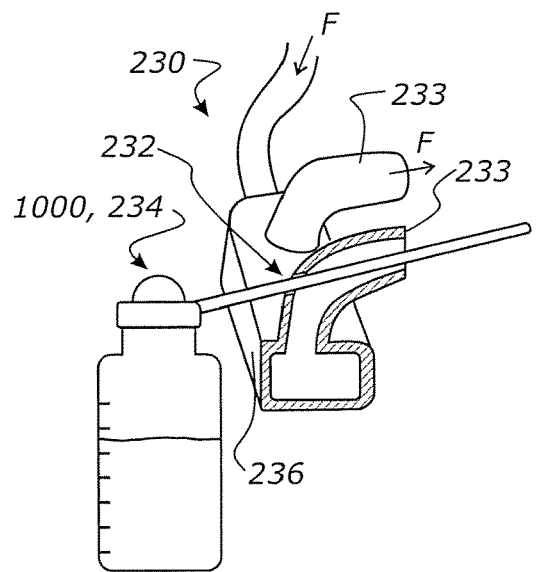
FIG. 24A shows a partial cross-section view of a cannula comprising a nasal prong with a port for accommodating access or insertion of a medicament dispenser into the flowpath of gases flowing through the nasal prong.

Alternatively, in still further embodiments, the port 232 may be provided upon one prong or as a feature of or integrated as a part of a pair of nasal prongs 233. For example, see FIG. 24A. For example, the port may be provided on a prong near a base of the prong.

In some configurations, the patient interface 230 may comprise of a shaped or otherwise moulded region 237 suitable for accepting or receiving or locating or seating of a medicament dispenser 234 or instrument 1000 to the interface 230. For example, in this manner a dispenser 234, such as a syringe, may be seated for greater or more accurate placement or control of its placement relative to the interface 230 which is located upon the user. A depression 237 in a manifold part 236 may be provided for such a seating or location of an instrument 1000 and/or a dispenser 234. For example, see FIGS. 23B and 23C. A depression 237 may act as a keyway to receive a corresponding key of the instrument or dispenser to correctly orientate the instrument or dispenser to the cannula. Alternatively, the interface may comprise a protrusion that provides a key to be received in a corresponding keyway of the instrument or dispenser.

In some configurations, the port comprises a closable opening 235 (e.g. shown in FIG. 23C), such as, but not limited to, a screw-cap or a push-fit cap. Alternatively, the port 232 may be a luer-type connection or may comprise of a valve that seals over an opening of the port 232 when the dispenser 234 is not connected or inserted. For example, a duck-bill type valve may be utilised to improve sealing or closure of the port 232 and to reduce likelihood of gas leaks from such a port 232.

Figure 23A:
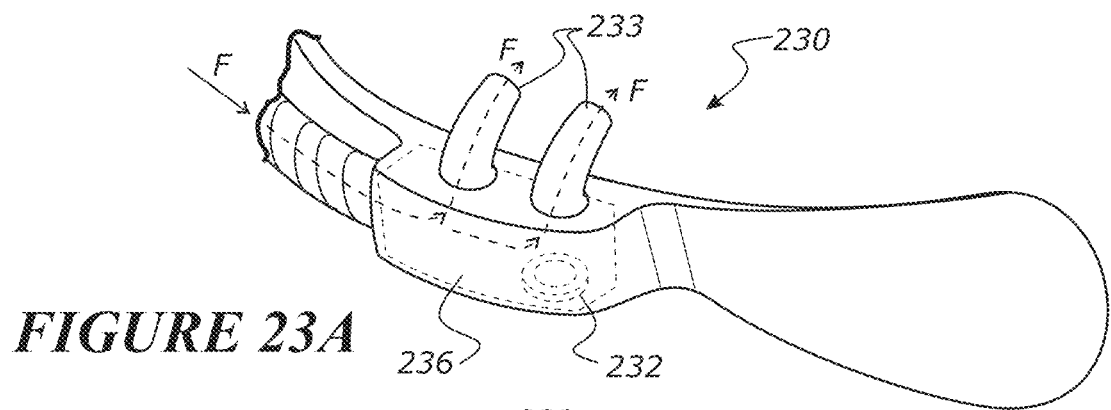
FIG. 23A illustrates a front partial perspective view of a nasal cannula interface including a port to which an instrument may be inserted.
Figure 23B:
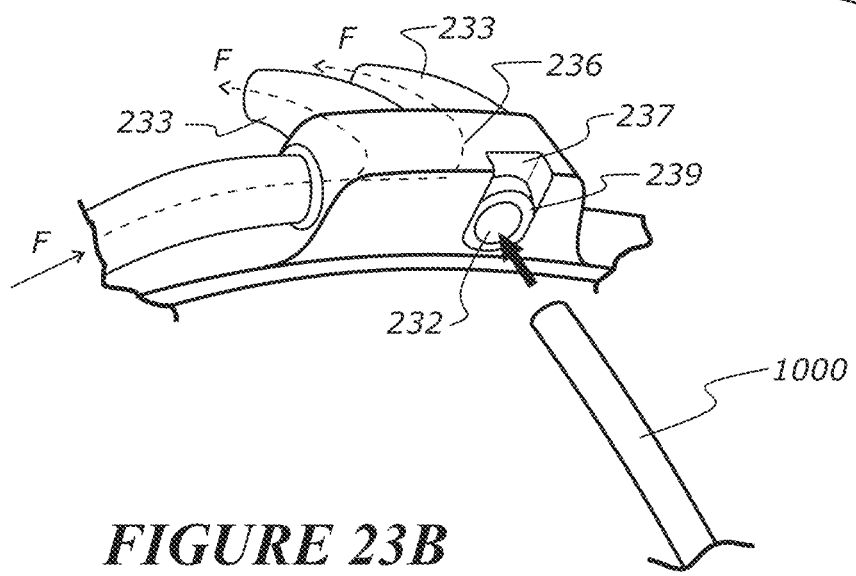
FIG. 23B illustrates an alternative arrangement and location of the portion of FIG. 23A, including a recess for receiving and locating an instrument.
Figure 23C:
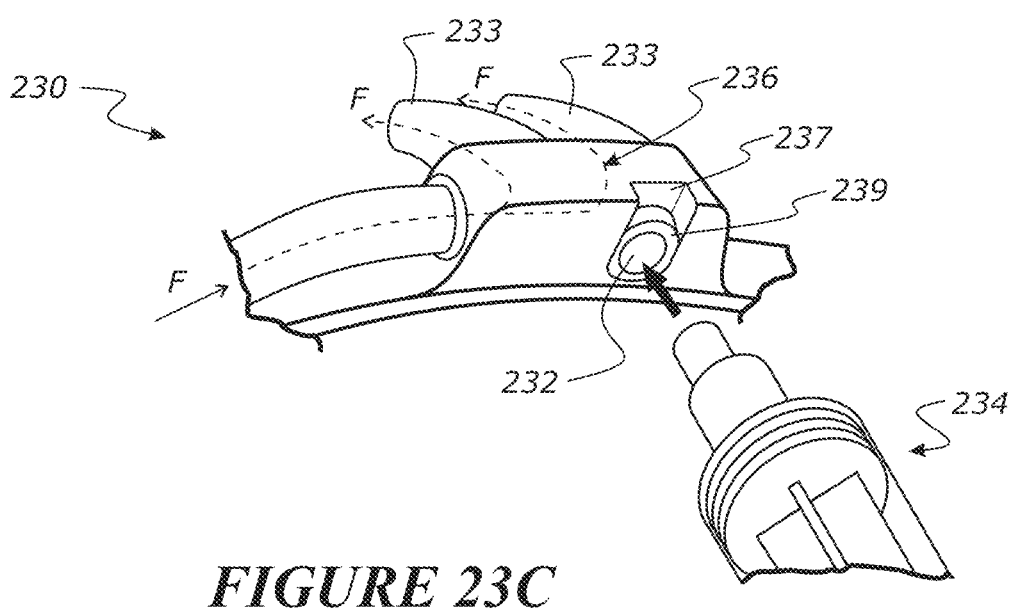
FIG. 23C provides the same view as 23B but shows a cannula including a recess for receiving and locating a medicament dispenser.
Figure 23D:
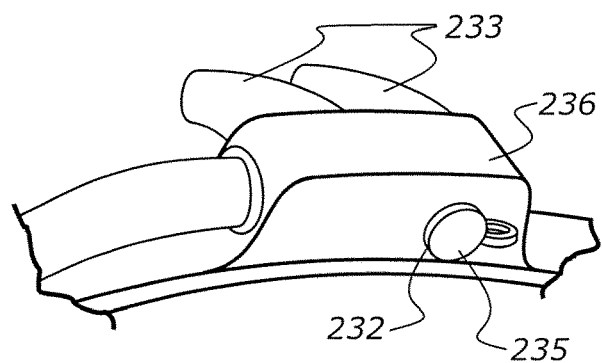
FIG. 23D illustrates a further alternative arrangement of a port on an interface, including a cap for sealing the port from the surrounding environment.
Figure 23E:
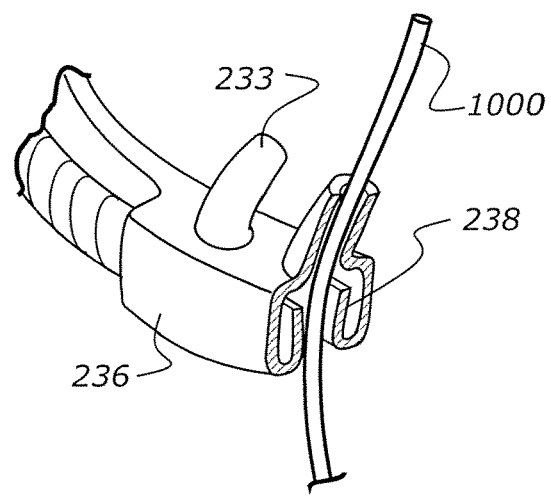
FIG. 23E illustrates an instrument in-situ with a port by way of a partial cross-sectional view.
Figure 23F:
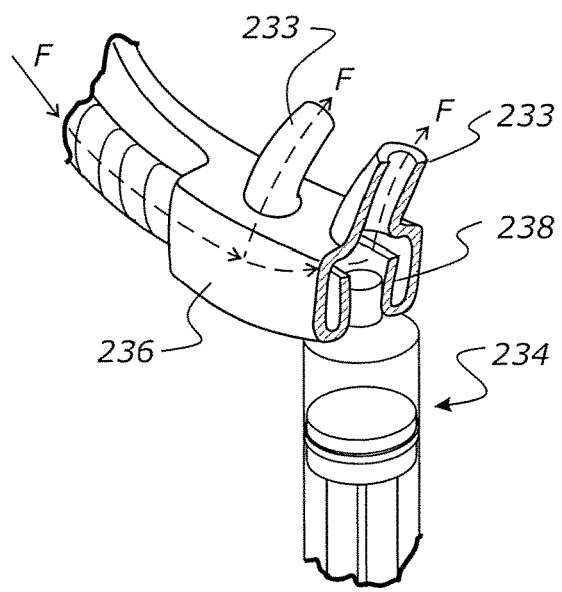
FIG. 23F shows a dispenser in-situ with a port by way of a partial cross-sectional view.

In some configurations, the port 232 may further comprise of a director or guide 238. The director or guide 238 may be used to direct an instrument more accurately, for example towards or up through a nasal prong 233, for example as shown in FIG. 23E. In some configurations, the director or guide may be a flow director or medicament director or guide. Such a director 238 may be used for directing dispensed medicament or a nozzle or outlet of a dispenser 234 more accurately, for example toward or up through one or more nasal prongs 233, to minimise the amount of medicament dispensed onto the interior side walls of the interface 230 or wall parts more associated with the port 232, which otherwise may not reach the user. Such a director or guide 238 may be a geometry of the port 232 or other protrusion shaped to direct the dispenser 4 or an outlet therefrom to a desired angle or position when in-situ with the port 2. For example, see FIG. 23F. With reference to FIG. 23F, the guide or director 238 (instrument or device director, or medicament director) may comprise a wall 238 extending from the port 232. The guide or director 238 may extend from the port 232 within a lumen or flowpath of the cannula 230. The guide or director 238 may extend from the port towards a nasal prong 233 within the flowpath of the cannula. The wall 238 may be an annular wall extending from the port through which the medicament or device or instrument passes into the flowpath of the cannula 230. For example, the guide may form a tubular structure extending from the port within the cannula. The guide 238 may be configured to provide a clearance between the guide 238 and the medicament delivery device 234 or the instrument 1000 to prevent or reduce friction between the guide and the medicament delivery device or the instrument as the medicament delivery device or the instrument is inserted into the cannula via the port 232. Further, in some configurations the port is configured to provide a clearance between the port and the medicament delivery device 234 or the instrument 1000. Therefore in some configurations the guide and the port do not rigidly hold the instrument or dispenser in a fixed position relative to the patient interface. The device may slide freely into the cannula (and possibly into the patient's airway) via the port and the guide. The guide or director 238 may be formed of a relatively rigid material to additionally form a relatively rigid component 239 (compared with other parts of the patient interface) to support an device or a dispenser, as described below.

In some configurations, the port 232 may provide for an opening which provides for a relatively rigid component 239 (compared with other parts of the patient interface) to support an device 1000 or a dispenser 234 (e.g. such as a syringe tip) upon insertion or entrance to the port 232 (such as a port provided upon a manifold). Such a relatively more rigid component 239 can allow for a user to apply a force against the port 232 while inserting an instrument or undertaking a dispensing of medicament (or at least configuring such a dispenser relative to the interface and/or user for subsequent dispensing a medicament). Provision of a relatively more rigid component 239 may assist in a positive and/or more defined or more secure location or a more positive seating of an instrument or a dispenser 234 to the interface 230 and port 232. A nasal cannula may comprise a resilient material for contacting the user, beneath the user's nose and/or the user's nares. For example nasal prongs are preferably formed of a resilient material to be inserted into the user's nares. In some embodiments, the relatively more rigid component is more rigid than the resilient material of the cannula. In some embodiments the rigid component 239 may be integrated into the cannula by overmoulding of the resilient material of the cannula.

In some configurations, the port comprising a relatively more rigid component provides for a pre-determined angle of insertion by the instrument or the dispenser to the port. In this manner, such a relatively rigid component requires a device (e.g. instrument or dispenser) to be successfully inserted to the port at a particular angle, such an angle may be that which may more accurately allow insertion of the instrument or dispenser or delivery of the medicament.

In some alternative configurations, the port 232 may comprise of a relatively softer or more flexible or compressible component that seals over the port 232 when not in use. Such a component can optionally provide for a seal about an instrument or a dispenser 234 or parts of the dispenser 234 (e.g. such as the tip of a syringe) when the instrument/dispenser 234 is inserted into the port 232. A seal may help minimise or reduce leaks between the device and the port 232 when they are operationally engaged, optionally particularly so during a medicament dispensing operation.

In some embodiments, the port 232 may be covered by a relatively elastic or elasticated cover material that stretches when the instrument/dispenser is inserted and allows extension. Such a cover may provide for a seal. A small cut or opening in the end of the elastic or elasticated cover is normally in a closed configuration and can seal the port 232 when relaxed, preventing leak; and when an instrument/dispenser is inserted into the port 232 and pushed through the elastic or elasticated cover, the cut or opening may be stretched over the end of the instrument/dispenser, thereby being opened sufficiently to allow for the instrument or dispenser to be inserted and/or medicament to be dispensed/deposited through it.

In still further alternative configurations, the port 232 may be formed of a relatively more rigid component or a material covered by, or surrounded by at least one layer of a relatively compressible material. In this manner, when the instrument or dispenser is inserted into the port 232, the relatively softer or compressible materials could be compressed or be conformable to the shape of the immediate surfaces of the instrument or dispenser, thereby assisting to promote a sealing around the instrument or dispenser. This can allow for the instrument or dispenser to remain substantially supported by the relatively more rigid component 239 or the structure underneath, yet provided with a sealing capability about a perimeter or other portion of the port 232 which becomes engaged or operatively in contact with the instrument or dispenser.

In some embodiments, the port 234 is adapted or configured to allow for a relatively long, thin instrument or medicament dispenser, such as a conduit or tube, to be inserted or to be ingressed into the port 232. Such a dispenser can then be extended to project along at least a length of or through the flowpath of the patient interface 230 or a component such as a gas supply conduit associated with the interface 230. Optionally, such a medicament dispenser may terminate at the outlet from one or more of said nasal prongs 233, alternatively such a medicament dispenser may terminate within the nasal cannula (i.e. upstream of the outlet from one or more nasal prongs) or may terminate at a position beyond the outlet of the one or more nasal prongs 233 (i.e. downstream of the outlet from the one or more nasal prongs). In some configurations outlet of the dispenser may terminate at a small distance beyond the outlet of a nasal prong downstream of the nasal cannula. For example, a small distance may be a distance that is less than an internal diameter of the outlet of the nasal prong, or less than twice the internal diameter of the outlet of the nasal prong, or a distance less than half the length of the nasal prong.

Figures 23G, 23H:
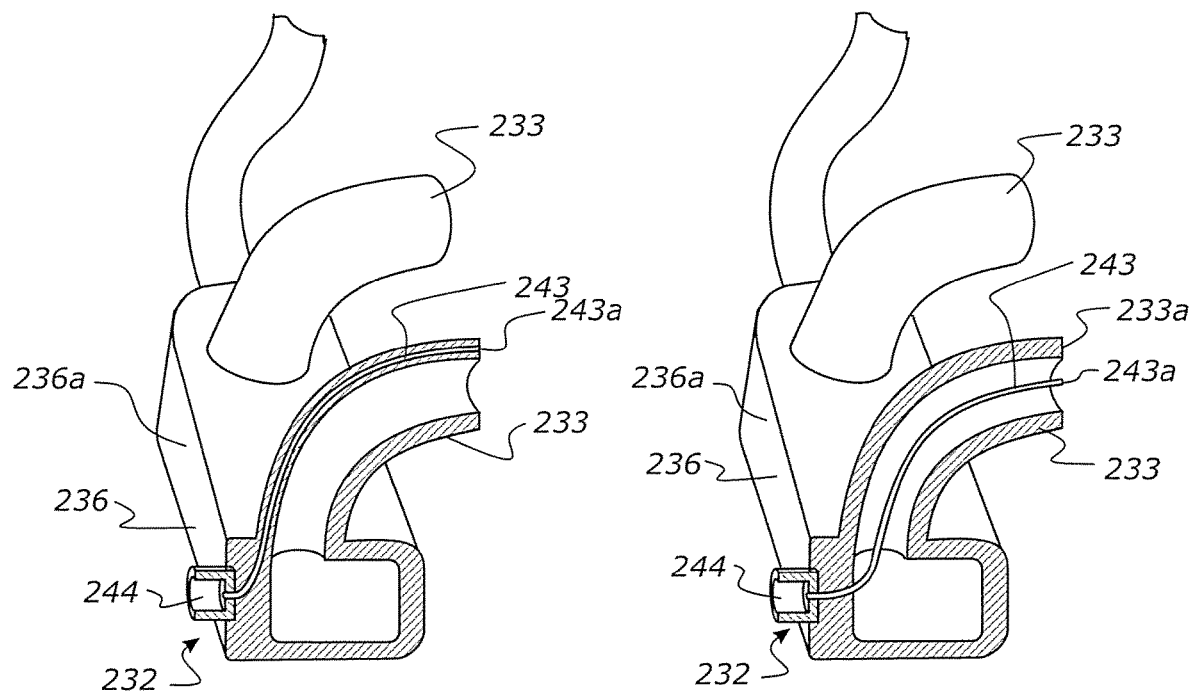
FIG. 23G shows a partial cross-sectional view of a cannula comprising a port and a medicament supply tube extending from the port to an outlet end of a prong of the cannula.
FIG. 23H shows a partial cross-sectional view of another cannula comprising a port and a medicament supply tube extending from the port to an outlet end of a prong of the cannula.

In some embodiments the nasal cannula may comprise a medicament supply tube that extends from the port so that medicament may be delivered further downstream from the port 232, for example, as illustrated in FIGS. 23G and 23H. The supply tube 243 may extend from the port 232 located at the manifold 236 of the nasal cannula to an outlet end 233a of the nasal prong 233, so that the medicament is dispensed from the cannula at or adjacent to an outlet of the prong into a patient's airway. As shown in FIG. 23G, in some embodiments the supply tube 243 may be formed within a wall of a nasal prong. For example, a supply tube may be over-moulded into the wall of a prong. The supply tube may be formed in a curved or otherwise shaped configuration prior to integration into the wall of the prong. In FIG. 23G the tube 243 is illustrated positioned along an upper side of the prong. In some embodiment the tube may be positioned in the wall of the prong to locate at least an outlet end of the tube towards an inward side of the prong, so that the outlet end of the tube is near or adjacent to the patient's septum in use. An inward side of a prong is a side of the prong that faces towards or bears against a patient's septum in use (or faces towards the other prong of the cannula). In some embodiments the tube 243 may be located along an inside wall surface of the prong, for example along an inside wall surface on an inward side of the prong.

In an alternative embodiment as shown in FIG. 23H, the supply tube 243 may be located or positioned within a lumen of the nasal prong, for example centrally within the prong so as to typically not press against a user's nare during use. The tube may be curved or otherwise shaped to follow or corresponding with a shape of the lumen of the prong. The port 232 may provide a recess 244 for receiving an outlet or nozzle of a dispenser to dispense medicament into the supply tube for delivery to the patient's airway. Alternatively, the port 232 may comprise a protrusion or male connector to be received within a nozzle or outlet of a dispenser. In some embodiments the port may be formed by an inlet end of the supply tube 243 to receive a nozzle or outlet of a dispenser. In some embodiments the port may be provided by an inlet end of the supply tube 243 that is to be received in a nozzle or outlet of a dispenser, such as an aerosol canister. The supply tube may extend from the manifold a distance so that the dispenser may be connected to the supply tube remotely from the manifold.

Figure 23I:
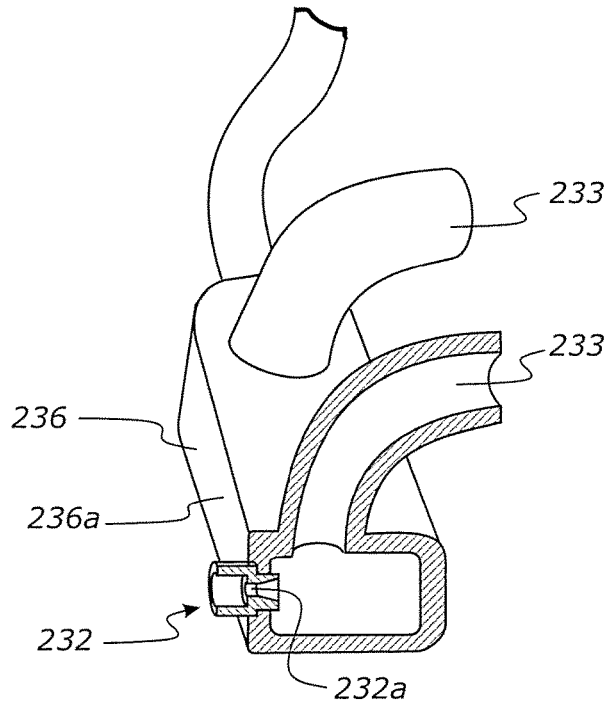
FIG. 23I shows a partial cross-sectional view of another cannula comprising a port with a small diameter outlet to assist with dispersing medicament.

As shown in FIGS. 23G to 23I, in a preferred embodiment the port 232 is provided on a wall of the cannula that faces away from the face of a patient in use. For example, in FIGS. 23G to 23I, the port 232 is provided on a front wall 236a of the manifold 236 of the cannula. The front wall is opposite to a rear wall that is in contact with or adjacent the upper lip or philtrum of the patient in use. With the port in a front wall of cannula the port is presented facing away from the patient's face is use, to provide unobstructed access to the port by a medical professional, for applying a dispenser to the port.

Preferably the supply tube 243 comprises a small diameter outlet 243a, such that the outlet operates as a nozzle or spray nozzle to assist with dispersing the medicament into a flowpath of the cannula or the patient's airway, either with or without a flow of gases provided by the cannula. For example, the supply tube may have an outlet with an internal diameter of less than 2 mm, or less than 1 mm. The diameter of the supply tube outlet is preferably substantially smaller than the internal diameter of a nasal prong. For example, the nasal prong may have an internal diameter of 4 mm or 5 mm or greater than 5 mm. The internal cross sectional area of the spray tube outlet may be less than 20% or 10% of the internal cross sectional area of the outlet of a nasal prong of the nasal cannula. In a preferred embodiment the tube 243 has a small diameter relative to the internal diameter of the nasal prong. In some embodiments the tube 243 has a constant cross section along its length. Preferably the spray tube is formed of a relatively rigid material to retain its shape during use, for example a curved shape to correspond with a curvature of the nasal prong 233.

Alternatively, in some further embodiments, connection or insertion of a dispenser to the port 232 may promote a protrusion (e.g. such as a lumen provided) to extend along and through one or more nasal prongs 233. In such a manner, there can be allowed for a deposition of a medicament further downstream from the port 232, or alternatively closer to the airway of a user. For example, if a long dispenser is instead used rather than a syringe tip (i.e. as was used in FIG. 23F).

Figure 23J:
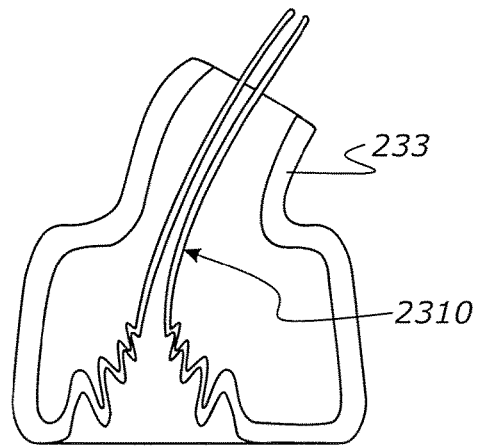
FIG. 23J shows a cross-sectional view of a nasal prong with an inner extendible protrusion or secondary nasal prong including corrugations or concertina-type arrangement.

In some embodiments, insertion of the dispenser may promote a protrusion 2310 to extend from the port 232 (e.g. at least as an extension through the nasal prong 233). See for example FIG. 23J, such a protrusion 2310 may be attached to the inside of the patient interface (e.g. the port 232 or an inner part of the interface, such as a manifold, or as a part of a nasal prong 233). Such a protrusion 2310 may comprise of corrugations or other concertina-type arrangements that can unfold and extend to allow an extension and the protrusion 2310 to extend beyond or past the end of one or a pair of nasal prongs 233, or other structures associated with a patient interface 230 so that the medicament may be deposited further into the user's airway, or at another preferred position along the flowpath of the cannula or user's airway. Such a protrusion can be an extendible lumen, optionally such a protrusion may be curved or shaped to fit comfortably into the nasal anatomy.

In some embodiments, when in an extended position, the protrusion 2310 allows for maintenance of the flowpath through the cannula or of a flow of gases to one or a pair of nasal prongs 233 of the cannula 230. In yet other embodiments, when in an extended position, the protrusion 2310 may engage with one or a pair of nasal prongs 233 or the flowpath to one or each said nasal prong 233 so as to block a flow of gases to one both nasal prongs of a pair of nasal prongs.

Figure 23K:
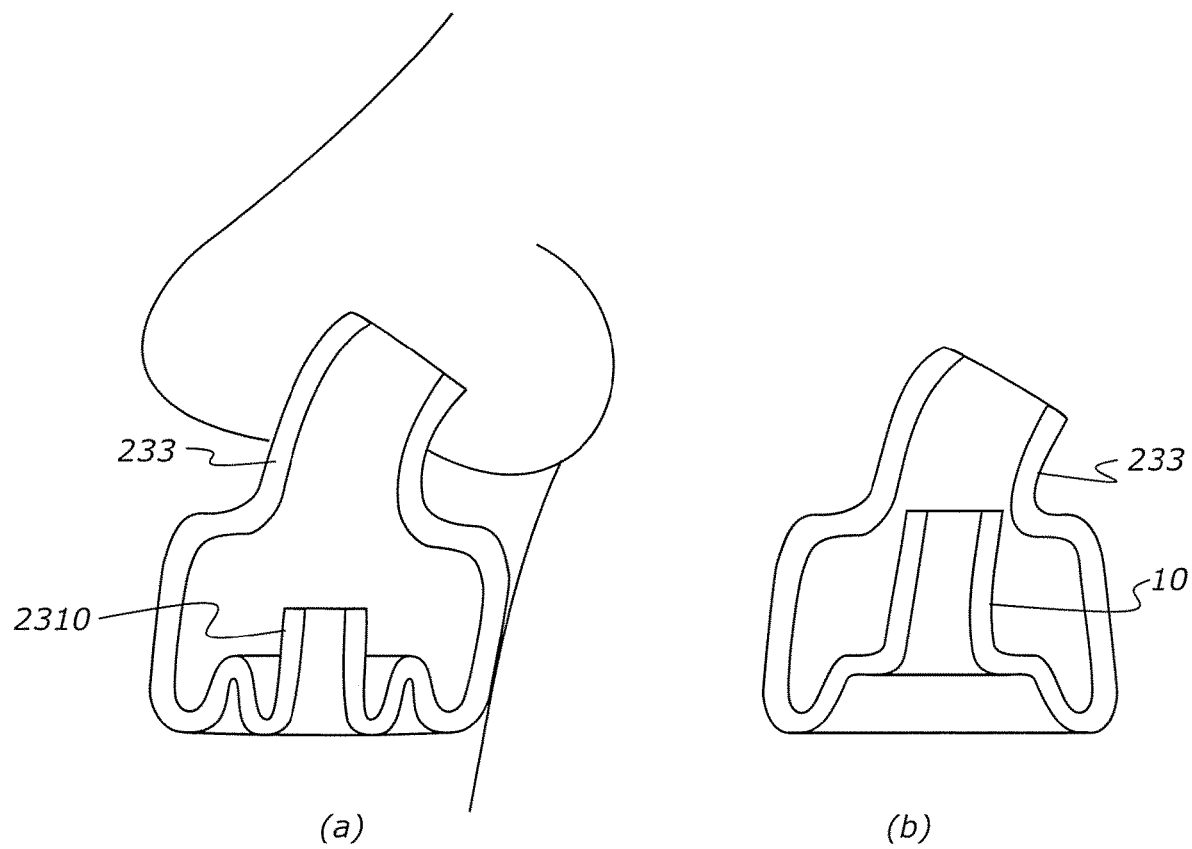
FIG. 23K shows a cross-sectional view of a nasal prong with an inner extendible protrusion or secondary nasal prong including corrugations or a concertina-type arrangement allowing for extension of the protrusion or secondary prong from a less extended position (FIG. 23K-a) and a more extended position (FIG. 23K-b)

Alternatively the insertion of the dispenser 234 may promote a protrusion 2310 to extend into a nasal prong 233 or a flowpath associated with a nasal prong, blocking the flow of gases to the user via that flowpath. See for example FIG. 23K. FIG. 23K-a shows a first configuration in which a protrusion 2310 is relatively unextended, while FIG. 23K-b shows a further configuration in which the protrusion 2310 is in a relatively more extended position. Such a configuration in which there is a reduced flow or a block entirely of a flowpath may be advantageous in situations where the delivered flow of gases (e.g. litres per minute) exceeds the user's inspiratory demand. In this case, excess gas flow escapes the nares during inspiration and medicament carried on this gas flow may be less effectively communicated to the user or may be wasted entirely and not directed to the user's airway. In some instances, medicament may be undesirably expelled into the room, such as a surgical theatre or pre-operative room. In this embodiment the flow of gases to the nasal prongs 233 can be blocked in the prong itself and thereby the prong stops delivering the gas—in this way, preferentially, only medicament will be directed to enter the user's nare (i.e. no gas flow). Blocking the flow may also allow the user to accurately control the deposition of the medicament into the patient's airway without interference from the flow of fluid. The gas flow from the blocked prong will exit through the other prong, or such gas flow may be relieved via a pressure relief valve or other arrangement or such device. Alternatively, the cannula may comprise a valve to block flow to the cannula when the dispenser is inserted. For example the cannula may comprise a valve with a valve element such as a flap that is moved to a closed position against a valve seat when the dispenser is inserted.

There may be a relatively high force required to cause the protrusion 2310 to extend. If the user wishes to allow high flow to continue during medicament delivery the user may insert the dispenser along the protrusion 2310 but not push so hard as to cause the protrusion to extend and block the flowpath through the cannula. The protrusion may be formed to tighten onto the dispenser when the dispenser is inserted into or through the protrusion. In this way, when the dispenser is retracted back through the protrusion to remove the dispenser from the nasal cannula the protrusion is pulled back to its original, unblocked position. For example, the protrusion may be formed from a soft/and or compressible or resilient material that tightens around the dispenser when inserted.

In some embodiments, a scavenging mechanism or system may be utilised in conjunction with the patient interface 230 as described herein. Such a system may be utilised to collect exhaled gases from a user, including exhaled medicament which has not been absorbed or taken-up by the user. Such a system may comprise a recirculation system including filtration, for re-delivery of the collected gases and medicament to the user. Such a mechanism attached to the patient interface could cover the user's mouth and/or nose to prevent medicament being exhaled back into a room. In particular, such a mechanism or system:

could use a one way valve attached to additional conduit that delivers that exhaled flow back to the system could allow the system to 'scrub' the excess medicament from the gas flow, thereby assisting in minimising wastage could be embodied in a face mask that is placed over a nasal cannula—such a face mask may be placed on the user during medicament delivery times.

In some embodiments, a nasal cannula may be designed to have one or both prongs 233 relatively long, such that they extend relatively deep into the user's nasal cavity. Optionally, one or both nasal prongs may be curved to conform to nasal geometry, for example this may allow for improved capabilities of successfully delivering administered medicament into the user's airway.

In various alternative configurations, one or both of a pair of nasal prongs may be extendable or comprises portions which are extendible in length, such as a protrusion 2310. For example, a nasal prong may comprise of an inner secondary prong portion, such as a protrusion 2310 which may comprise of corrugations or concertina-type sections which can be extended to lengthen and allow such a secondary prong to project further than a main nasal prong into a user's airway. Such an extended secondary prong may be utilised as a protrusion for improved for extending of the flowpath for delivery of medicament to a user's airway. In various instances, see FIG. 23J as an example, the prongs may utilise such a secondary prong that can be extended when the user wants to deliver a medicament, or when the user is asleep and can tolerate greater discomfort. Longer prongs may also have the additional benefit of creating greater flushing of the airway and potentially further reducing $CO_2$ from a user's airways.

Figure 24B:
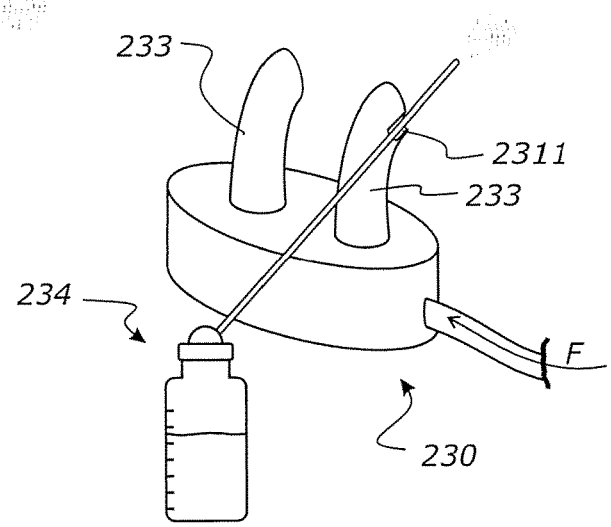
FIG. 24B shows a perspective view of an alternative cannula comprising a nasal prong with a channel in an outer surface of the prong for insertion of a dispenser.

In some embodiments, the port 232 may be a guiding channel or other shaped accommodation region for allowing improved access to the nares by a dispenser 234 without affecting the delivery of respiratory support. For example, the port may be a channel 203 in an outer surface of the prong as described above with reference to FIG. 19B, one or both nasal prongs 233 shaped to accommodate the shape of a dispenser 234 or at least the dispensing tip of a dispenser. For example see FIG. 24B. Alternatively, a nasal prong 233 may comprise a port 232 or accommodation region 233 through which a dispenser 234 may be inserted for delivery of medicament to the gas flow F and/or into a user's airway—see for example FIG. 24A.

In some configurations there is a pre-formed medicament dispenser pre-loaded with medicament for use with the patient interface as described above.

In some embodiments, the dispenser 234 may be preformulated with a pre-determined quantity of medicament in a ready-to-dispense configuration. For example, lignocaine may be provided in a dispenser 234 in a pre-determined quantity for administration to a user.

In some embodiments, the dispenser may be provided with the cannula to ensure correct fit with the port(s). Or an attachment/adaptor may be provided to fit to existing dispensers, for example to attach to the end of a syringe.

In some embodiments, the patient interface 230 may comprise of a reservoir 2312 for receiving and/or storing of a medicament. In other embodiments, the reservoir 2312 may be actuated manually or by other forms (e.g. such as by an electronic dosing or administration arrangement which allows for release of the medicament from the reservoir into the flowpath for delivery to the user). The reservoir may be permanently attached and refillable by the user, or be detachable and attached when desired.

Where the dispensing of medicament may be manually actuated by a user, this may for example be by way of a button on the interface or by depressing a syringe plunger. Such actuation can allow for the release of the medicament from the reservoir 2312.

Figure 25A:
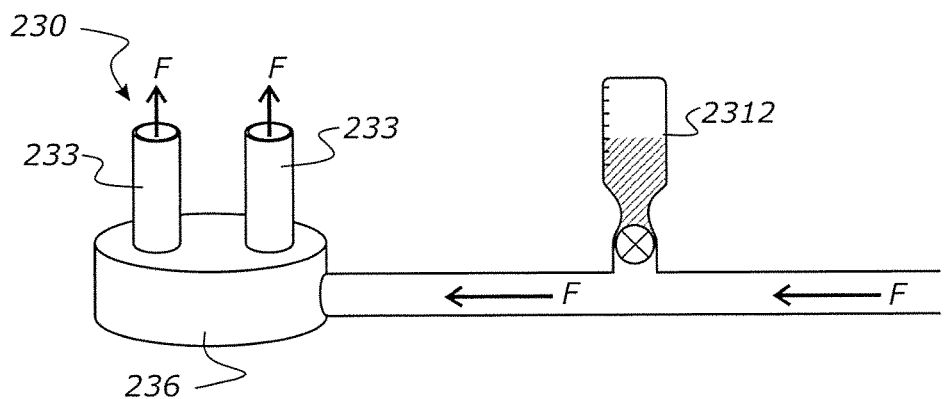
FIGS. 25A, 25B show a reservoir provided in association with a gas supply conduit for supplying gas to a patient interface, the medicament being released into the flowpath of the gas (FIG. 25A shows medicament stored in the reservoir, FIG. 25B shows the medicament having been released).
Figure 25B:
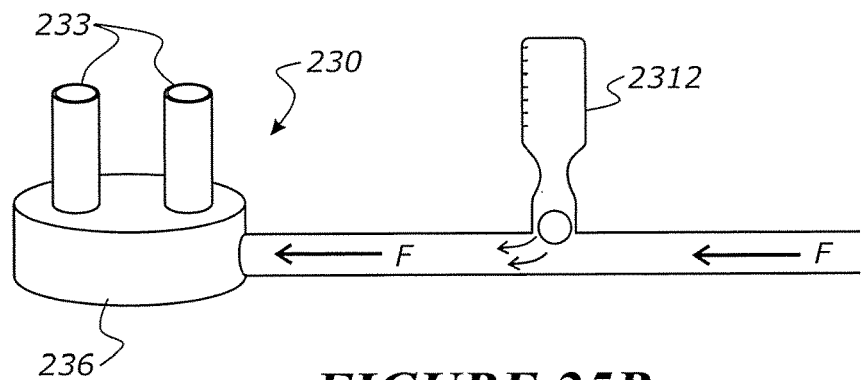
Figure 26A:
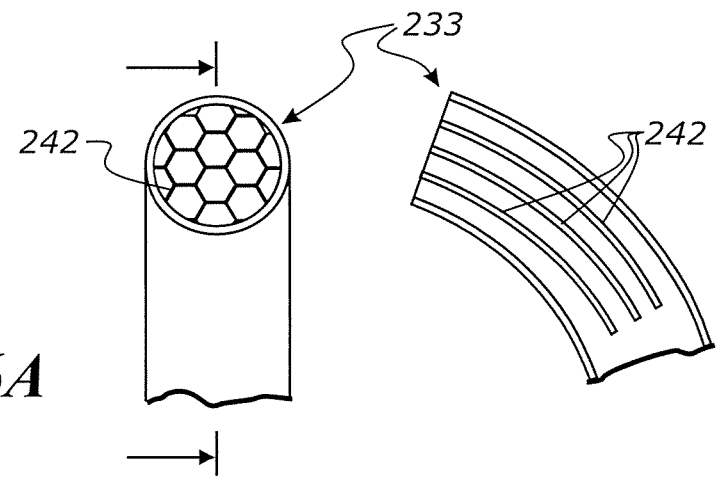
FIG. 26A shows an end view and a cross sectional side view of a nasal prong, and FIGS. 26B and 26C each show a cross sectional side view of a nasal prong, the nasal prongs of these Figures comprising internal walls/partitions or structures to divide a lumen and/or outlet of the prongs.
Figure 26B:
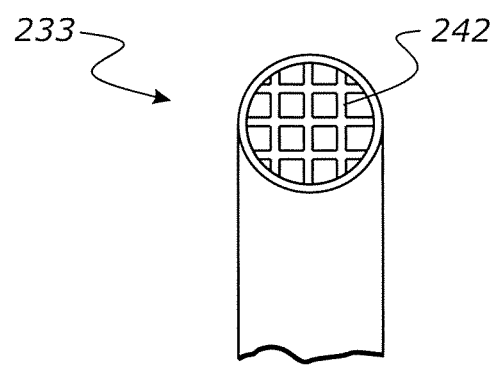
Figure 26C:
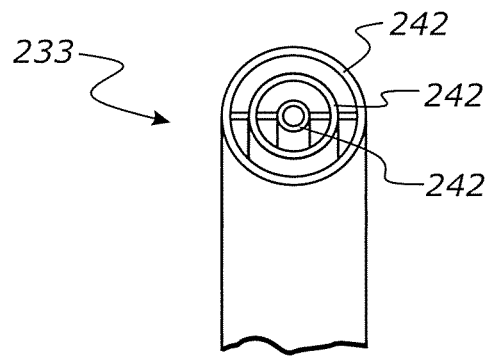
Figure 27:
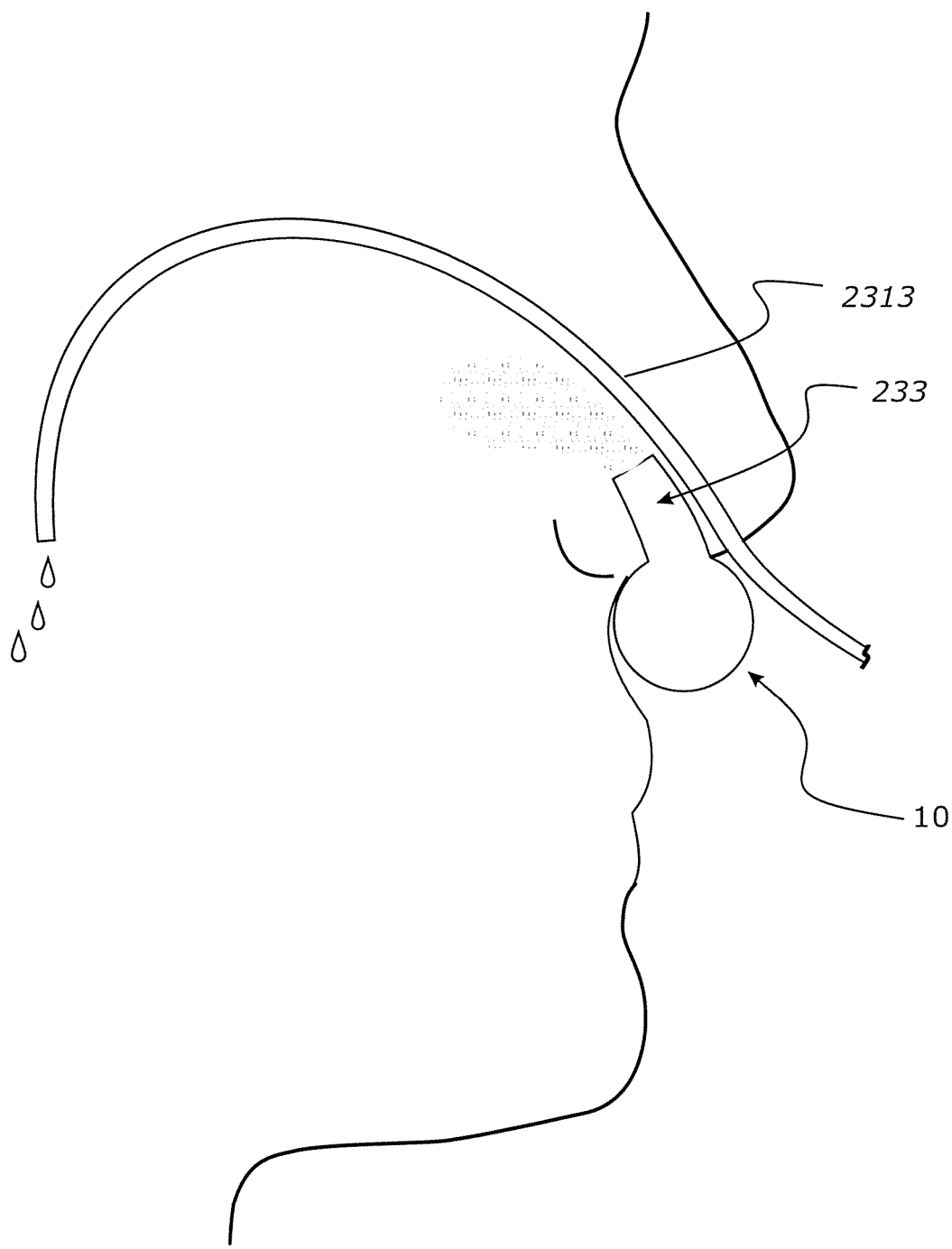
FIG. 27 shows an arrangement where a relatively long tube or conduit may be utilised to separately dispense or direct a medicament into the airway of a user's, when a nasal prong in in-situ.

In one example, actuation may result in the medicament being forced or encouraged to release out of reservoir and into the flowpath of the interface or a flowpath associated with the interface (e.g. that of a gas supply conduit). For example in FIG. 25A the reservoir enables medicament to be delivered into the flow F of gases being directed to a user's airway; while FIG. 25B shows the medicament having been released into the flow and being directed toward the interface 230. The reservoir may be made of a non-rigid material that may be squeezed to force the medicament to open a valve and release the medicament into the flow path of the conduit. The valve may be biased to a normally closed position so that the valve closes when the reservoir is not squeezed to force the valve open.

As high gas delivery flow rates may be used, the medicament may be carried in the gas stream to the user's airway.

For example, according to those various embodiments and configurations described herein, a flow rate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100 L/min, about 70 to 80 L/min).

Such relatively high flowrates of gases may assist in providing the supplied gases into a user's airway, or to different parts of a user's airway, for example such flowrates may allow for a delivery of such gases to the upper, middle or lower airway regions.

Such relatively high flowrates can assist to, in combination with a medicament delivered to the flowpath or the flow of gases being delivered to the user, provide assisted delivery of medicament to a user's airway, or different parts of a user's airway. For example, such relatively high flowrates may effectively help drive or push medicament further into a user's airways than under normal respiratory conditions by the user.

Figure 28:
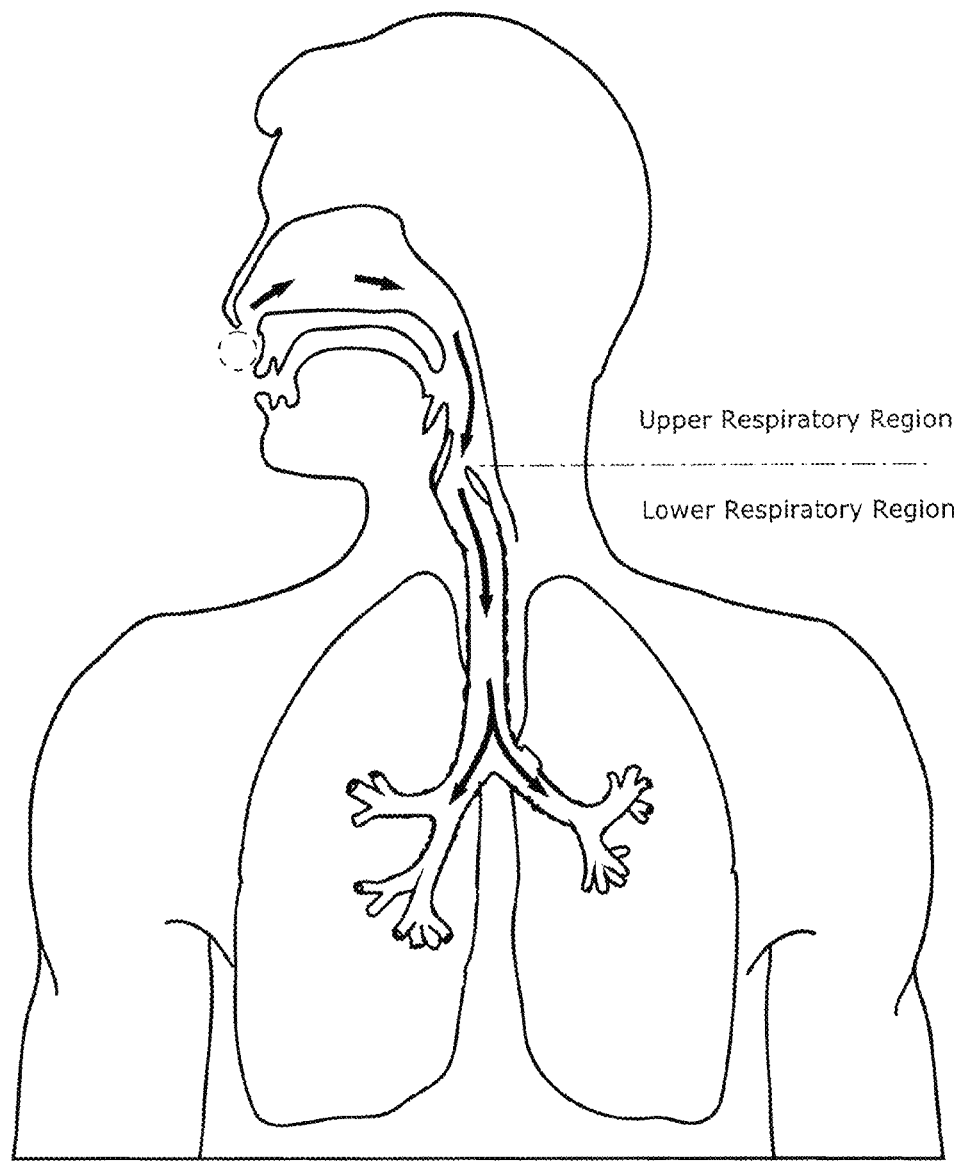
FIG. 28 shows a generalised diagram of a respiratory tract, including the upper respiratory region and the lower respiratory region.

FIG. 28 shows a typical airway of a person, and includes arrows to indicate the path of how a relatively high flowrate of gases supplied to a user may be utilised to effectively push or drive the supplied gases further or deeper into a user's airway than when the person is under normal or typical self-driven respiratory conditions.

If liquid medicament is used, the gas flow may help to partially nebulise the medicament into smaller particles that can carry further down the airway. A valve may be provisioned to sit between the reservoir and a main gas supply conduit, such that the valve is normally closed. However, actuation of the reservoir may be used to put the valve under pressure (e.g. by squeezing or button actuation (not shown)) with the valve consequently opening and allowing the medicament to be made available for release into the gas stream (see FIG. 25B)

In alternative configurations, the medicament in the reservoir 2312 may be released or made available to the flowpath by actuation of a negative pressure in the flowpath, thereby opening a valve or other member which may be sealing the reservoir from the flowpath. For example, if the patient were asked to inhale deeply a valve or seal can be opened and medicament released. The valve or seal may be designed such that normal tidal breathing does not create enough negative pressure to open it. In this way medicament delivery can also be timed with inspiration, avoiding wastage and encouraging the medicament to travel further down the airway particularly when the patient inhales deeply.

In still further embodiments, where a valve or seal is used to close off the reservoir, the aperture of the valve may be designed to be small and create nebulised particles of a certain size that enable medicament delivery to a specific location.

In other configurations, details of the above embodiments could be applied here as well however the medicament may be delivered via another channel, not necessarily through the nasal prongs. Such a channel may be sized differently to the prongs e.g. may have a smaller internal diameter to create high gas/medicament velocities and effectively jet medicament further down the user's airway than the prongs might otherwise be able to achieve. The channel could use gas delivered via a sidestream or other source of gas from the main gas flow, a separate gas flow or from another pressurized source, for example an aerosol canister, or may not deliver gas and only be used as a medicament delivery port. In this manner:

- there could be multiple channels for delivery of medicament (e.g. different medicament through each separate channel).
- a different medicament could be delivered through each channel, or prong, at the same time.
- flow through each channel/prong could be independently controlled to manage each medicament concentration or administration separately.

In other configurations, the port 232 that dispenses the medicament (e.g. whether the port is located on the patient interface or as a port on a conduit associated with the gas flow) could be designed so that when liquid medicament is dispensed through it, the medicament is atomised. For example, inside one or each nasal prong 233 there could be serrations/ribs or walls/partitions 242 as shown in FIGS. 26A and 26C, and/or the opening or outlet of the nasal prong could be made of many small apertures instead of a single one large outlet, as shown in FIGS. 26A and 26B. Forcing or directing liquid through such features may assist in breaking the liquid up into small droplets with a lower weight than a large liquid bolus. Alternatively, such structures as shown in FIG. 26A to 26C may cover only a portion of the cross-sectional area of the prong or prong outlet.

According to the configuration above, reducing particle size of the medicament being dispensed to a user can aid the medicament to be carried in the gas flow and delivered to the user. For example, the force of a depressed syringe containing liquid medicament or an automated piston, depressing the medicament through the features could be used to create the atomization or nebulisation (i.e. turning the medicament into particles or reducing medicament particle size). As such, nebulised or reduced particle sizes could be sized to target deposition at the larynx, or other desired locations depending on the target for the medicament.

In some configurations, the port 232 on the interface 230 could comprise a single aperture but sized so as to cause nebulisation or atomization of liquid medicament when it is administered into and dispensed therefrom (i.e., the port may have a relatively small exit aperture through which dispensed medicament must pass, e.g. less than 1 mm diameter). For example, as shown in FIG. 23I, the port may comprise a small diameter outlet 232*a* so that as medicament is dispensed from a medicament delivery device into the port 232 the medicament is atomized or sprayed into the flow path of the nasal cannula, for example into the manifold of the cannula. In the case of a nasal cannula, one of the prongs 3 may have a relatively small inner diameter or include serration/ribs or the opening or outlet of the nasal prong could be made of many small apertures instead of a single one large outlet so as to effect such an in-line atomisation or nebulisation of medicament, as described above with reference to FIGS. 26A to 26C.

In some configurations, the reservoir 2312 may be provided as a part of the patient interface, or may be associated with a gas supply conduit (e.g. that conduit supplying gas to the patient interface) or may be provided as a reservoir at a source device for providing a gas flow to the patient interface. It will be appreciated the medicament may be delivered via main gas path or could be provided via a separate conduit up to interface.

Dispensation of medicament can be controlled via mechanically actuated valve or by software. (e.g. mechanical actuation or may be electronically controlled).

In various configurations, the delivery or dispensing of medicament can be timed to coincide with a user's inspiration, or a part of the inspiratory phase, to avoid wastage during exhalation phase of breath. As such, delivery of medicament may be timed to occur at the peak of inspiration to ensure the most flow possible is travelling down the user's airway and to encourage deep deposition. For example, if medicament delivery was desired during inspiration a population average of inspiratory pressures could be determined and a valve associated with the reservoir designed to open at pressures below this value. Medicament could be actuated by a pressure in a main gas conduit, or if a separate line was run next to the main gas conduit and terminated in the user's nares, then this could also be triggered in a similar way.

Alternatively, the inspiration phase could be detected by measuring the interface pressure or pressure at some place in the system and the medicament delivery could be activated (e.g. by opening a valve, controlled by software) when the pressure falls below a pre-determined value, such as the (rolling) average. A pressure below the average pressure would indicate the user is causing a reduction in the pressure in the system and is therefore inspiring. The average could be calculated over a set number of breaths (e.g. 5 breaths) or time (e.g. 1 minute).

In other configurations, if the medicament delivery conduit does not have gas flow through it the release of medicament could be activated via an additional electrically activated piston or other release system. Alternatively, delivery could be timed to activate with a certain inspiratory flow rate that matches a flow most likely to carry the medicament down the airway to deposit at the vocal cords (or other desired location). More specifically, if the medicament were delivered as part of the main gas flow, the gas flow could also be controlled to meet inspiratory demand to avoid wastage of medicament with high flow rates in excess of the inspiratory demand and to ensure delivery of the correct amount of medicament.

In yet other configurations:

- High flow rates may be used to deliver dry powder medicaments. This may be desirable for depositing medicament in the nasal airway where blood flow is high and medicament may be quickly absorbed into the blood stream via the thin epithelium layer.

An anti-coagulant may be added to powders. This may prevent the powder from caking and potentially blocking the medicament delivery port. This may be particularly important when the powder is delivered via a humidified gas conduit.

Alternatively the powder may be delivered via a separate conduit that may use the same gas source as the main gas supply, or a side-stream supply of it, but is not humidified.

Delivery via other airway equipment may be utilised, for example an attachment could be fitted to end of a laryngoscope to allow for delivery of medicament into a user's airway without requiring an additional medicament delivery device (e.g. atomiser or nebulisers etc.).

Still further, in other configurations it may be possible to:

Coat the medicament in a chemical that has a half life that degrades after set time (e.g. if it is known that at 70 litre per minute it takes 0.5 seconds for flow to reach the larynx, use a coating that will degrade sufficiently after 0.5 s).

Coat the medicament in a chemical that degrades on contact with preferential tissue or materials, such as vocal cord tissue. For example, the vocal cords epithelium is stratified squamous epithelium. This type of epithelium is also present in the oral cavity and the nasal vestibule; however the rest of the conducting portion is lined by respiratory epithelium. If medicament is delivered via a nasal cannula, this avoids the oral cavity. If the delivered medicament is delivered at sufficient velocity and in a manner directed past the nasal vestibule, the majority of it should get past the nasal vestibule. Hence it may pass down to the vocal cords before coming in contact with any other stratified squamous epithelium, and deposit at this location.

Nasal prong length could be extendable or adjustable for delivery of medicament further into airway. For example, with corrugations at the base of a nasal prong, similar to FIG. 23J. Again a dispenser (e.g. a syringe r other forms of a dispenser) could be inserted into the prong, and in doing so, could activate the prong length extension.

The flow rate could be adjusted for a short time (e.g. one breath, or part of a breath) during medicament deposition, to encourage deposition on the larynx. For example, the flow rate could be increased for a short time to increase flow velocity and jet medicament further down the airway. This could be timed with inspiration to help medicament flow down the airway. Or, it may be found that the current flow rate (e.g. 70 lpm) may cause the medicament to be deposited too far down the airway, so the flow may need to be reduced when medicament deposition is desired/activated. Flow rate may be adjusted manually by a user as medicament is dispensed.

The medicament polarity could be determined, or the medicament could be electrically polarised to be attracted to magnets. A magnet could be placed behind the user's neck while supine at the position of the desired medicament deposition location to attract the medicament to deposit there as it travels down the airway.

Another embodiment is explained in FIG. 27. In this case the delivered gas flow may help to force the liquid medicament onto the back of the laryngeal wall as it travels down. FIG. 27 shows an arrangement where a relatively long tube or conduit 2313 may be utilised to separately dispense or direct a medicament delivered from a dispenser or a reservoir (not shown) into the airway of a user, when a nasal prong 233 of a patient interface 230 is simultaneously also in in-situ with a nare or nares.

In further configurations:

Medicament could be delivered as (gas-filled) bubbles. Bubbled delivered through prongs or additional medicament delivery channel. Prong diameter, or medicament channel diameter could be sized to control the diameter of the bubbles and encourage deposition at the larynx, or other location.

Medicament bubbles could be delivered orally. The airway has a decreasing cross-section diameter as it extends towards the vocal cords from the mouth if the patient's mouth is open wide. Thus if the patient is asked to keep their mouth open and the bubble diameter is the same size as the trachea at the position of the vocal cords, the bubbles may travel down the airway and burst only at the vocal cords as they come into contact with an area the same size as them, depositing the medicament there.

The medicament could be delivered via a coaxial conduit. The liquid medicament is pushed along the outer layer and flow is passed through the centre. The liquid medicament may form a film over the end of the conduit (e.g. prongs) when no flow is passed through it. When flow is re-started this may allow a bubble to form at the end and be pushed along with the gas stream. As an example, if two conduits are used (e.g. separate gas supply to a pair of nasal prongs) the flow may be delivered alternately through each conduit and a film may be able to form over the other conduit when flow is not delivered. Bubbles can thus be delivered alternately from each conduit/prong.

Bubbles may be filled with a composition of gases that target deposition in a certain location. For example helium, nitrogen, and/or oxygen may be used to create a stokes number that targets deposition on the vocal cords taking account of the flow rate, medicament composition and particle drag, and oral/nasal anatomy.

In further configurations:

Once a user is reclined the medicament may delivered via a liquid bolus (rather than aerosolized).

If the bolus is delivered while the patient is supine the effect of gravity may allow the medicament to flow down the back of the throat to the vocal cords.

The foregoing description of the invention includes preferred forms thereof. Modifications may be made thereto without departing from the scope of the invention.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples only.

What is claimed is:

1. A nasal cannula configured to deliver a flow of fluid to a user, the nasal cannula comprising:

a manifold part, the manifold part having an inlet configured to receive the flow of fluid, and at least one outlet configured to deliver the flow of fluid to one or both of the user's nares, wherein the at least one outlet comprises at least one non-sealing patient interface, wherein the manifold part includes a patient-contacting surface and the inlet is located on a lateral side of the manifold part adjacent the patient-contacting surface; and a port located on the manifold part, the port configured to perform at least one of: delivering a medicament into the flow of fluid being delivered by the nasal cannula to the user, or interfacing with a medicament delivery device, wherein the port comprises an opening, the opening being at least one of closable or re-closable, and wherein the non-sealing patient interface comprises a non-sealing nasal prong that extends proximally, a path through the port being aligned with a flow path through the nasal prong of the nasal cannula.

2. The nasal cannula as claimed in claim 1, wherein the port comprises a guide for directing a flow of medicament into the flow of fluid, or for directing the medicament delivery device into at least one of the nasal cannula or the user's airway.

3. The nasal cannula as claimed in claim 2, wherein the guide provides for a pre-determined geometry of the port to direct, locate, or position the medicament delivery device, or an outlet of the medicament delivery device, at a desired angle or orientation relative to the nasal cannula.

4. The nasal cannula as claimed in claim 1, wherein the port extends from the manifold part to the nasal prong of the nasal cannula, or wherein the nasal cannula further comprises a second port and a second non-sealing nasal prong, the port and the second port extending from the manifold part to the nasal prong and the second nasal prong respectively.

5. The nasal cannula as claimed in claim 1, wherein the port is arranged to face away from the user's face when in use.

6. The nasal cannula as claimed in claim 1, further comprising a moulded or otherwise shaped region configured for accepting, receiving, locating, or seating of the medicament delivery device relative to the port.

7. The nasal cannula as claimed in claim 1, wherein with the medicament delivery device in-situ with the port, the port seals about the medicament delivery device.

8. The nasal cannula as claimed in claim 1, wherein the port comprises of a seal, the seal being self-closing.

9. The nasal cannula as claimed in claim 1, wherein the port comprises a rigid component configured to support the medicament delivery device when in-situ with the port.

10. The nasal cannula as claimed in claim 1, wherein the nasal cannula or the port comprises a plurality of in-line atomisation or nebulisation of medicament dispensers, the plurality of in-line atomization or nebulization of medicament dispensers configured to deliver medicament via the port.

11. The nasal cannula as claimed in claim 10, wherein the plurality of in-line atomization or nebulization of medicament dispensers comprise a plurality of ribs or serrations within a nasal prong of the nasal cannula.

12. The nasal cannula as claimed in claim 1, further comprising a medicament supply tube extending from the port.

13. The nasal cannula as claimed in claim 12, wherein the supply tube is formed within a wall of the nasal prong of the nasal cannula or located within a lumen of the nasal prong.

14. The nasal cannula as claimed in claim 12, wherein an inlet end of the supply tube is located at the port or extends from the port so as to allow the medicament delivery device to be connected to the port remotely from the manifold part.

15. The nasal cannula as claimed in claim 12, wherein the supply tube comprises a small diameter outlet such that the outlet operates as a nozzle to spray or otherwise disperse the medicament from the supply tube.

16. The nasal cannula as claimed in claim 1, wherein the port is adapted to receive a nozzle or an outlet of the medicament delivery device or to be received in the nozzle or the outlet of the medicament delivery device.

17. The nasal cannula as claimed in claim 1, wherein the port is located on a side of the manifold part opposite another side of the manifold part where the at least one outlet is located.

18. The nasal cannula as claimed in claim 1, wherein the nasal cannula is configured to perform one or more of:
  delivering the flow of fluid to the user to provide high flow support;
  delivering the flow of fluid at a flow rate of above 15 L/min; or
  delivering the flow of fluid that comprises a humidified gases flow.

19. A nasal cannula configured to deliver a flow of fluid to a user, the nasal cannula comprising:
  a manifold part, the manifold part having an inlet configured to receive the flow of fluid, and at least one outlet configured to deliver the flow of fluid to one or both of the user's nares, wherein the at least one outlet comprises at least one non-sealing patient interface, wherein the manifold part includes a patient-contacting surface and the inlet is located on a lateral side of the manifold part adjacent the patient-contacting surface; and a port located on the manifold part, the port configured to perform at least one of: delivering a medicament into the flow of fluid being delivered by the nasal cannula to the user, or interfacing with a medicament delivery device, wherein with the medicament delivery device in-situ with the port, the port seals about the medicament delivery device, and wherein the non-sealing patient interface comprises a non-sealing nasal prong that extends proximally, a path through the port being aligned with a flow path through the nasal prong of the nasal cannula.

20. A nasal cannula configured to deliver a flow of fluid to a user, the nasal cannula comprising:
  a manifold part, the manifold part having an inlet configured to receive the flow of fluid, and at least one outlet configured to deliver the flow of fluid to one or both of the user's nares, wherein the at least one outlet comprises at least one non-sealing patient interface, wherein the manifold part includes a patient-contacting surface and the inlet is located on a lateral side of the manifold part adjacent the patient-contacting surface; and a port located on the manifold part, the port configured to perform at least one of: delivering a medicament into the flow of fluid being delivered by the nasal cannula to the user, or interfacing with a medicament delivery device, wherein the port comprises of a seal, the seal being self-closing, and wherein the non-sealing patient interface comprises a non-sealing nasal prong that extends proximally, a path through the port being aligned with a flow path through the nasal prong of the nasal cannula.

* * * * *